United States Patent
Martini et al.

(10) Patent No.: US 10,451,482 B2
(45) Date of Patent: Oct. 22, 2019

(54) DETERMINATION OF COLOR CHARACTERISTICS OF OBJECTS USING SPATIALLY MODULATED LIGHT

(71) Applicant: Palo Alto Research Center Incorporated, Palo Alto, CA (US)

(72) Inventors: Joerg Martini, San Francisco, CA (US); Marshall W. Bern, San Carlos, CA (US); Noble M. Johnson, Menlo Park, CA (US); Peter Kiesel, Palo Alto, CA (US); Doron Kletter, San Mateo, CA (US); Bowen Cheng, Atherton, CA (US); Michael I. Recht, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 234 days.

(21) Appl. No.: 14/181,571

(22) Filed: Feb. 14, 2014

(65) Prior Publication Data

US 2015/0276486 A1  Oct. 1, 2015

(51) Int. Cl.
*G01J 3/51* (2006.01)
*G01N 15/14* (2006.01)
*G01N 15/10* (2006.01)

(52) U.S. Cl.
CPC ............. *G01J 3/51* (2013.01); *G01N 15/147* (2013.01); *G01N 15/1429* (2013.01); *G01N 15/1434* (2013.01); *G01N 15/1475* (2013.01); *G01N 15/1459* (2013.01); *G01N 2015/1006* (2013.01);

(Continued)

(58) Field of Classification Search
CPC ..... G01J 3/51; G01N 15/1459; G01N 15/147; G01N 15/1475; G01N 15/1474
See application file for complete search history.

(56) References Cited

U.S. PATENT DOCUMENTS

| | | |
|---|---|---|
| 4,037,965 A | 7/1977 | Weiss |
| 4,172,227 A | 10/1979 | Tyrer et al. |
| 4,441,816 A | 4/1984 | Hencken et al. |

(Continued)

FOREIGN PATENT DOCUMENTS

| | | |
|---|---|---|
| EP | 1950552 | 7/2008 |
| WO | WO0194938 | 12/2001 |
| WO | WO2005017969 | 2/2005 |

OTHER PUBLICATIONS

File History for U.S. Appl. No. 14/246,893.

(Continued)

*Primary Examiner* — Violeta A Prieto
(74) *Attorney, Agent, or Firm* — Hollingsworth Davis, LLC

(57) ABSTRACT

A system is configured to determine a color distribution of an object moving along a flow direction relative to a spatial filter. The light emanating from the object is time modulated according to the mask features of the spatial filter. First and second detectors are arranged to sense the modulated light. The first detector senses light having a first wavelength spectrum and generates a first electrical output signal in response to the sensed light. The second detector light senses light having a second wavelength spectrum and generates a second electrical output signal in response to the sensed light. Signals from the first and second detectors include information about color distribution of the object.

19 Claims, 23 Drawing Sheets

(52) U.S. Cl.
CPC ............ *G01N 2015/1447* (2013.01); *G01N 2015/1472* (2013.01); *G01N 2015/1477* (2013.01)

(56) References Cited

U.S. PATENT DOCUMENTS

| | | | |
|---|---|---|---|
| 4,596,254 | A | 6/1986 | Adrian et al. |
| 5,392,776 | A | 2/1995 | Thurston et al. |
| 5,682,038 | A | 10/1997 | Hoffman |
| 5,778,878 | A | 7/1998 | Kellam |
| 6,213,579 | B1 | 4/2001 | Cornell et al. |
| 6,649,416 | B1 | 11/2003 | Kauer et al. |
| 6,654,521 | B2 | 11/2003 | Sheng et al. |
| 7,104,634 | B2 | 9/2006 | Weksler et al. |
| 7,291,824 | B2 | 11/2007 | Kiesel et al. |
| 7,358,476 | B2 | 4/2008 | Kiesel et al. |
| 7,386,199 | B2 | 6/2008 | Schmidt et al. |
| 7,420,677 | B2 | 9/2008 | Schmidt et al. |
| 7,471,393 | B2 | 12/2008 | Trainer |
| 7,471,399 | B2 | 12/2008 | Kiesel et al. |
| 7,479,625 | B2 | 1/2009 | Kiesel et al. |
| 7,502,123 | B2 | 3/2009 | Kiesel et al. |
| 7,547,904 | B2 | 6/2009 | Schmidt et al. |
| 7,688,427 | B2 | 3/2010 | Cox et al. |
| 7,701,580 | B2 | 4/2010 | Bassler et al. |
| 7,763,856 | B2 | 7/2010 | Kiesel et al. |
| 7,817,254 | B2 | 10/2010 | Hegyi et al. |
| 7,817,276 | B2 | 10/2010 | Kiesel et al. |
| 7,894,068 | B2 | 2/2011 | Bassler et al. |
| 7,961,326 | B2 | 6/2011 | Martini et al. |
| 8,082,015 | B2 | 12/2011 | Yodh et al. |
| 8,153,949 | B2 | 4/2012 | Kiesel et al. |
| 8,153,950 | B2 | 4/2012 | Kiesel et al. |
| 8,203,711 | B2 | 6/2012 | Shinoda |
| 8,373,860 | B2 | 2/2013 | Kiesel et al. |
| 8,388,569 | B2 | 3/2013 | Uhland et al. |
| 8,437,582 | B2 | 5/2013 | Kiesel |
| 8,594,470 | B2 | 11/2013 | Kiesel et al. |
| 8,629,981 | B2 | 1/2014 | Martini et al. |
| 8,723,140 | B2* | 5/2014 | Kiesel ............... G01N 21/6408 250/458.1 |
| 8,842,259 | B2 | 9/2014 | Garey |
| 8,921,277 | B2 | 12/2014 | Kiesel et al. |
| 9,029,800 | B2* | 5/2015 | Kiesel .................. G01J 3/36 250/458.1 |
| 9,074,978 | B2 | 7/2015 | Lo et al. |
| 9,114,606 | B1* | 8/2015 | Ready .................. B41J 2/0456 |
| 9,134,221 | B2* | 9/2015 | Lo ..................... G01N 15/1459 |
| 9,207,066 | B2* | 12/2015 | Martini ................ G01B 11/046 |
| 9,261,452 | B2 | 2/2016 | Martini et al. |
| 9,629,981 | B2 | 4/2017 | Thungana et al. |
| 2003/0203502 | A1 | 10/2003 | Zenhausern et al. |
| 2003/0235924 | A1 | 12/2003 | Adams et al. |
| 2004/0067137 | A1 | 4/2004 | Moroso |
| 2004/0226386 | A1 | 11/2004 | Gysling et al. |
| 2007/0076210 | A1 | 4/2007 | Kiesel et al. |
| 2007/0145249 | A1 | 6/2007 | Kiesel et al. |
| 2007/0146704 | A1 | 6/2007 | Schmidt et al. |
| 2007/0146888 | A1 | 6/2007 | Schmidt et al. |
| 2007/0147728 | A1 | 6/2007 | Schmidt et al. |
| 2008/0181827 | A1 | 7/2008 | Bassler et al. |
| 2008/0183418 | A1 | 7/2008 | Bassler et al. |
| 2008/0186488 | A1 | 8/2008 | Kiesel et al. |
| 2008/0186492 | A1 | 8/2008 | Kiesel et al. |
| 2008/0186504 | A1 | 8/2008 | Kiesel et al. |
| 2009/0156917 | A1 | 6/2009 | Martini et al. |
| 2009/0190121 | A1 | 7/2009 | Hegyi et al. |
| 2009/0195773 | A1 | 8/2009 | Kiesel et al. |
| 2009/0195852 | A1* | 8/2009 | Bassler ............... G01N 21/645 359/238 |
| 2010/0201988 | A1 | 8/2010 | Kiesel |
| 2010/0225913 | A1 | 9/2010 | Trainer |
| 2011/0222062 | A1* | 9/2011 | Martini ................ G01N 21/05 356/417 |
| 2012/0194590 | A1 | 8/2012 | Suzuki |
| 2012/0236291 | A1 | 9/2012 | Pittaro et al. |
| 2013/0016335 | A1 | 1/2013 | Lo et al. |
| 2013/0037726 | A1 | 2/2013 | Kiesel et al. |
| 2013/0037728 | A1 | 2/2013 | Kiesel et al. |
| 2013/0083315 | A1* | 4/2013 | Lo ............................ G01J 3/46 356/73 |
| 2014/0152986 | A1 | 6/2014 | Trainer |
| 2014/0192359 | A1* | 7/2014 | Martini ................ G01N 21/05 356/417 |
| 2014/0370612 | A1* | 12/2014 | Bassler ............... G01N 15/147 436/94 |
| 2015/0105295 | A1 | 4/2015 | Kiesel et al. |
| 2015/0177118 | A1 | 6/2015 | Johnson et al. |
| 2015/0185139 | A1 | 7/2015 | Kiesel et al. |
| 2015/0233703 | A1* | 8/2015 | Martini ................ G01B 11/043 356/28 |
| 2015/0233704 | A1* | 8/2015 | Martini ................ G01B 11/046 356/635 |
| 2015/0276387 | A1* | 10/2015 | Kletter ............... G01N 15/1429 250/226 |
| 2015/0276486 | A1 | 10/2015 | Martini et al. |
| 2015/0280290 | A1 | 10/2015 | Saha et al. |
| 2015/0285622 | A1* | 10/2015 | Kiesel .................... G01B 11/14 604/500 |

OTHER PUBLICATIONS

Kiesel et al., "Spatially Modulated Fluorescence Emission from Moving Particles", Appl. Phys. Lett. 94, 2009, pp. 041107-1-041107-3.
Kiesel et al., "Spatially Modulated Emission Advances Point-of-Care Diagnostics", Laser Focus World, Nov. 2010, pp. 47-50.
U.S. Appl. No. 14/155,094, filed Jan. 14, 2014, Martini et al.
Petersson et al., "Free Flow Acoustophoresis: Micorfluidic-Based Mode of Particle and Cell Separation", Anal. Chem, 79 (14), 2007, pp. 5117-5123.
Yamada et al., "Pinched flow fractionation: continuous size separation of particles utilizing a laminar flow profile in a pinched microchannel", Anal. Chem. 76 (18), Sep. 2004, pp. 5465-5471. (abstract only).
Yamada et al., "Microfluidic Particle Sorter Employing Flow Splitting and Recombining", Anal. Chem. 78, 2006, pp. 1357-1362.
Ji et al., "Silicon-based microfilters for whole blood cell separation", Biomed Microdevices 10(2), 2008, pp. 251-257. (abstract only).
Schrum et al., "Microchip Flow Cytometry Using Electrokinetic Focusing", Anal. Chem. 71 (19), Oct. 1999, pp. 4173-4177. (abstract only).
Huh et al., "Microfluidics for flow cytometric analysis of cells and particles" Physiol. Meas. 26 (3), Jun. 2005, pp. R73-R98. (abstract only).
Fu et al., "Electrokinetically driven micro flow cytometers with integrated fiber optics for on-line cell/particle detection", Analytia Chimica Acta, Vo. 507 (1), Apr. 2004, pp. 163-169. (abstract only).
Lee, Gwo-Bin et al., "Micromachine-based multi-channel flow cytometers for call/particle counting and sorting", J. Micromech, Microeng. 15 (2005) 447-454. (abstract only).
Lin et al., "Vertical focusing device utilizing dielectrophoretic force and its application on microflow cytometer", Journal of Microelectromechanical Systems, vol. 13, No. 6, Dec. 2014, 10 pages.
Zhu et al., "Dielectrophoretic focusing of particles in a microchannel constriction using DC-biased AC electric fields", Electrophoresis, vol. 30 (15), Jul. 2009. (abstract only).
Chu et al., "A three-dimensional (3D) particle focusing channel using the positive dielectrophoresis (pDEP) guided by a dielectric structure between two planar electrodes", Lab on a Chip, Issue 5m 2009, pp. 688-691. (abstract only).
Chang et al., Three-dimensional hydrodynamic focusing in two-layer polydimethylsiloxane (PDMS) microchannels, J. Michromech. Microeng 17, 2007, pp. 1479-1486.
Sheng et al., "Digital holographic microscope for measuring three-dimensional particle distributions and motions", Applied Optics, Vo. 45 (16), Jun. 2006, pp. 3893-3901.

(56) References Cited

OTHER PUBLICATIONS

Lindken et al., "Stereoscopic micro particle image velocimetry" Experiments in Fluids, 41, 2006, pp. 161-171.
Pereira et al., "Microscale 3D flow mapping with µDDPIV", Experiments in Fluids, vol. 42 (4), Apr. 2007, pp. 589-599. (abstract only).
Cheong et al., "Flow Visualizaiton and Flow Cytometry with Holographic Video Microscopy", Optics Express 17, 2009, pp. 13071-13079.
Lima et al., "Confocal micro-PIV measurements of three dimensional profiles of cell suspension flow in a square microchannel", Measurement Science and Technology, vol. 17, 2006, pp. 797-808.
Pugia et al., "Microfluidic Tool Box as Technology Platform for Hand-Held Diagnostics", Clinical Chemistry, vol. 51 (10), 2005, pp. 1923-1932.
File History for U.S. Appl. No. 13/206,436.
File History for U.S. Appl. No. 12/024,490.
File History for U.S. Appl. No. 12/762,702.
File History for U.S. Appl. No. 13/113,021.
U.S. Appl. No. 14/181,560, filed Feb. 14, 2014, Kletter et al.
U.S. Appl. No. 14/181,530, filed Feb. 14, 2014, Martini et al.
U.S. Appl. No. 14/181,524, filed Feb. 14, 2014, Martini et al.
File History for U.S. Appl. No. 14/246,912.
File History for EP App. No. 15153858.4 as retrieved from the EP Electronic File System on Aug. 5, 2016, 117 pages.
File History for U.S. Appl. No. 14/181,560.
File History for U.S. Appl. No. 14/181,524.
File History for U.S. Appl. No. 15/209,450.
File History for U.S. Appl. No. 14/181,530.

\* cited by examiner

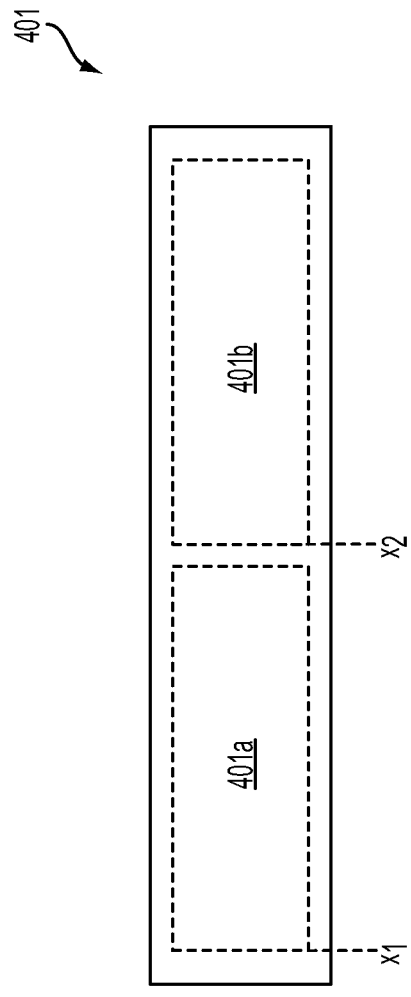
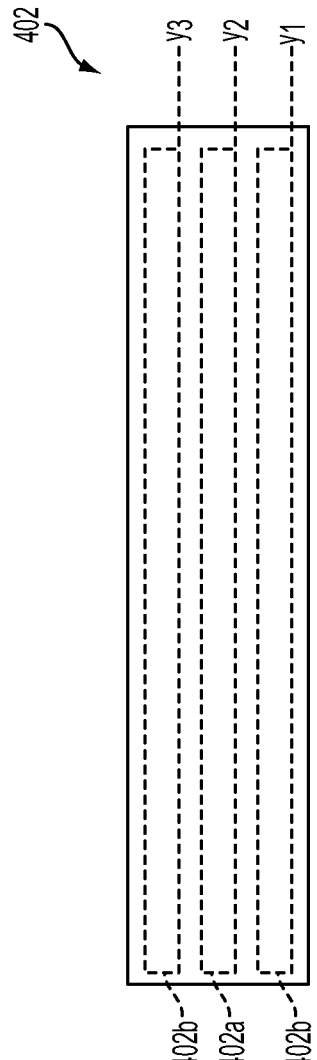
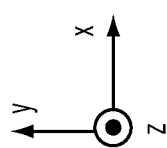
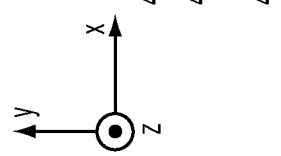

DETERMINATION OF COLOR CHARACTERISTICS OF OBJECTS USING SPATIALLY MODULATED LIGHT

STATEMENT REGARDING FEDERALLY SPONSORED RESEARCH AND DEVELOPMENT

This invention was made with government support under contract number W911NF-10-1-0479 (3711), awarded by the Department of Defense. The U.S. Government has certain rights in this invention.

TECHNICAL FIELD

This application relates generally to techniques for performing sample analysis by evaluating light emanating from the objects in a sample. The application also relates to components, devices, systems, and methods pertaining to such techniques.

BACKGROUND

The present disclosure relates generally to techniques that determine object characteristics using light emanating from the objects. More specifically, the techniques can use filter arrangements to allow for the transmission, reflection, fluorescence, phosphorescence, photoluminescence, chemoluminescence and/or scattering of light with time variation, such as where the objects are moving relative to the filter arrangements.

Various techniques have been proposed for using light emanating from objects. For example, U.S. Pat. No. 7,358,476 (Kiesel et al.) describes a fluidic structure with a channel along which is a series of sensing components to obtain information about objects traveling within the channel, such as droplets, cells, viruses, microorganisms, microparticles, nanoparticles, or other objects carried by fluid. A sensing component includes a set of cells that photosense a range of photon energies that emanate from objects. A processor can receive information about objects from the sensing components and use it to obtain spectral information. Additional techniques are described, for example, in U.S. Patent Application Publications 2008/0181827 (Bassler et al.) and 2008/0183418 (Bassler et al.) and in U.S. Pat. No. 7,701,580 (Bassler et al.), U.S. Pat. No. 7,894,068 (Bassler et al.), U.S. Pat. No. 7,547,904 (Schmidt et al.), U.S. Pat. No. 8,373,860 (Kiesel et al.), U.S. Pat. No. 7,420,677 (Schmidt et al.), and U.S. Pat. No. 7,386,199 (Schmidt et al.).

SUMMARY

Some embodiments involve a device comprising a spatial filter having a plurality of mask features and extending along a flow direction, light emanating from at least one object moving along the flow direction, an intensity of the emanating light being time modulated according to the mask features. A first detector is positioned to sense a first portion of light emanating from the object, the first portion of light having a first wavelength range. The first detector is configured to generate a first electrical signal in response to the sensed first portion of light. A second detector is positioned to sense a second portion of the emanating light, the second portion of light having a second wavelength range different from the first wavelength range. The second detector is configured to generate a second electrical signal in response to the second portion of light, wherein the first and second signals include information about color distribution of the object.

According to some aspects, a first optical filter is arranged in a path of the emanating light and between the object and the first detector. The first optical filter is configured to substantially transmit the first wavelength range to the first detector and to substantially block wavelengths other than the first wavelength range from reaching the first detector.

According to some aspects, the second portion of light comprises light scattered by the object.

In some implementations, a second optical filter is arranged in a path of the emanating light and between the object and the second detector. The second optical filter is configured to substantially transmit the second wavelength range to the second detector and to substantially block wavelengths other than the second wavelength range from reaching the second detector.

In some arrangements the system includes an analyzer configured to determine the color distribution based on a difference between the first signal and the second signal.

According to some aspects, the information includes information about at least one of an amount or type of color inhomogeneity of the object. The type of color inhomogeneity may include one or more of a symmetric color distribution, an asymmetric color distribution, a separated color distribution, and a granular color distribution.

Some arrangements include an analyzer configured to develop a first derivative signal comprising a derivative of an amplitude of the first electrical signal with respect to time and a second derivative signal comprising a derivative of an amplitude of the second electrical signal with respect to time and to determine at least one of the amount or type of color inhomogeneity of the object based on the first and second derivative signals.

Some arrangements include an analyzer configured to perform a cross-correlation of the first electrical signal and the second electrical signal and to determine at least one of the amount or type of color inhomogeneity of the object based on the cross correlation.

Some embodiments involve a device that includes a spatial filter having a plurality of mask features and extending along a flow direction, light emanating from at least one object moving along the flow direction, an intensity of the emanating light being modulated according to the mask features. A first detector is positioned to sense a first portion of light emanating from the object, the first portion of light having a first wavelength range, the first detector configured to generate an electrical signal in response to the sensed first portion of light. A second detector is positioned to sense a second portion of the emanating light, the second portion of light having a second wavelength range different from the first wavelength range, the second detector configured to generate a second electrical signal in response to the second portion of light. The first and second signals include information about the color characteristics of the object. In some implementations, the characteristics of the object include color distribution of the object.

The object may include at least first and second color regions and the first signal includes information about a length along the flow direction of the first color region and the second signal includes information about a length along the flow direction of the second color region.

According to some implementations, the first signal includes information about a width or thickness of the first color region along a direction perpendicular to the flow direction and the second signal includes information about a width or thickness of the second color region along the direction perpendicular to the flow direction.

Some embodiments involve a method that includes sensing light emanating from an object moving with respect to a spatial filter, the emanating light modulated according to mask features of the spatial filter. A first electrical signal is generated in response to sensing a first portion of the emanating light having a first wavelength range. A second electrical signal is generated in to sensing a second portion of the emanating light having a second wavelength range. The first and second electrical signals include information about color characteristics of the object.

According to some aspects a difference signal comprising a difference between the first electrical signal and the second electrical signal is developed.

In some implementations, the amplitude of the first and second signal are differentiated with respect to time. Color inhomogeneity of the object is analyzed based on the differentiated signals. In some implementations, time locations of the signal peaks of the differentiated first and second signals and determined. The color characteristics are analyzed based on the locations of the signal peaks.

For example, the color characteristics may include one or more of a symmetric color distribution, an asymmetric color distribution, a separated color distribution, and a granular color distribution.

Some embodiments are directed to a device that includes a spatial filter having a plurality of mask features and extending along a flow direction, the mask features including first features having a first optical transmission characteristic and second features having a second optical transmission characteristic, light emanating from at least one object moving along the flow direction, an intensity of the emanating light being modulated according to the first mask features and the second mask features. A detector is positioned to sense the light emanating from the object and to generate an electrical output signal in response to the sensed light, wherein the electrical output signal includes information about the color distribution of the object.

According to some aspects, the electrical output signal includes information about one or more of a length along the flow direction and width or thickness along a direction perpendicular to the flow direction for each of at least two color regions of the object, the first color region emanating light transmitted by the first mask features and the second color region emanating light transmitted by the second mask features.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein:

FIGS. 4A-4C illustrate several configurations for color spatial filters;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1A:
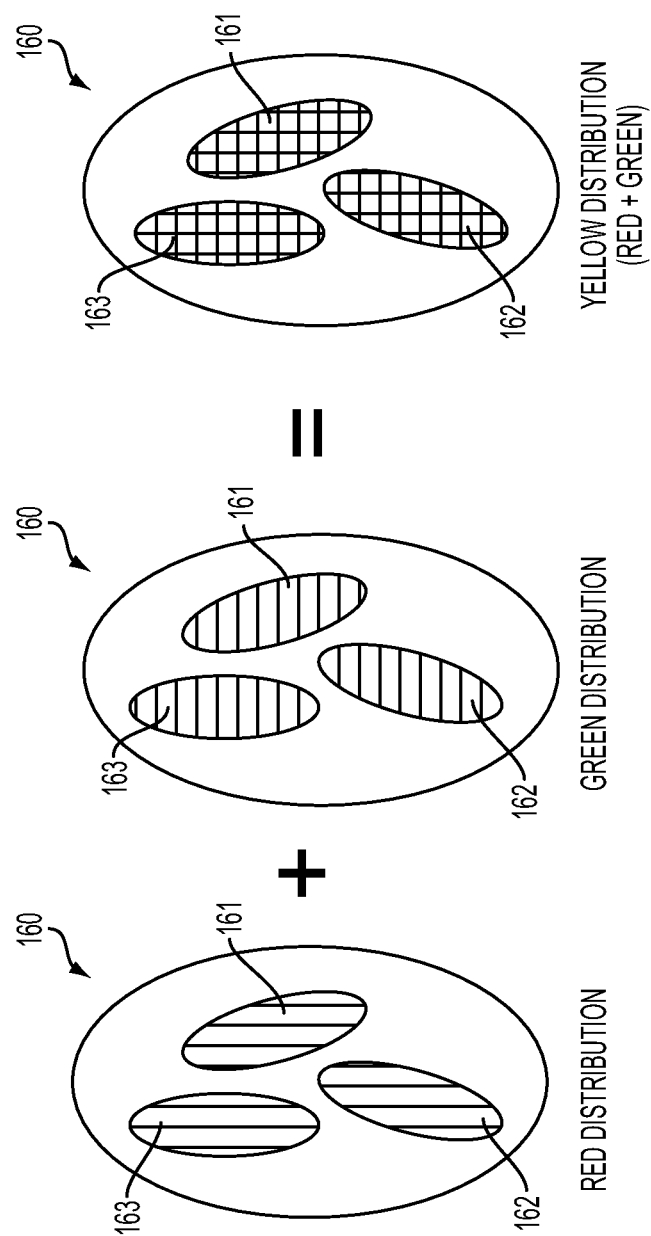
FIGS. 1A and 1B exemplify color distribution of light emanating from an object.

Various techniques have been proposed for using light emanating from objects to determine object characteristics such as size, charge, porosity, surface characteristics, and elasticity. Light emanating from an object exhibits a distribution of wavelengths. The human perception of the wavelength distribution is classified as "color" in the visible wavelength range. Depending on the origin of the emanating light, different spectral regions or colors may be emanating from an object. For example, an object illuminated with monochromatic light may show Mie scattering of that light in various directions. The Mie-scattered light has the same wavelength than the incident light. Additionally, the incident light may excite fluorescence in the object. Fluorescence light may include a relatively broad band of wavelength, may include a relatively narrow band of wavelengths, or may include discrete spectral lines. The fluorescence wavelengths are generally at higher wavelength than the incident light. Other light emanating phenomena that show wavelength or color characteristics include: Up-conversion, second harmonic generation, multi-photon excited fluorescence, Raman scattering, phosphorescence, absorption etc.

The light emanating properties of objects are not necessarily homogeneous as discussed below. For example, light absorption properties vary for chlorophyll containing cells because chloroplasts appear green to the human perception while other parts of the cell may appear black (uniformly absorbing) or transparent. Objects may have a color spatial distribution that can be important for analysis purposes including for identifying the object type.

There are different types of color spatial distribution that can occur in objects. For example, natural color spatial distributions can be present in chlorophyll containing cells. As another example, color spatial distributions may be artificially created such as by Gram staining of bacteria. In many implementations, functional staining is a standard procedure in life sciences and many functional assays that rely on functional staining have been developed and are commercially available.

Numerous methods may be used to selectively couple stains or dyes of different color to (bio-)molecules, cells, cell sub-structures, DNA, specific proteins etc. These methods include fluorescent staining as a popular scientific method in microscopy and cytometry. As one example, DAPI may be used to stain the cell's nucleus and TRITC-conjugated phalloidin may be used to stain the cell's actin filaments. Understanding the color spatial distribution of objects or within regions of objects can aid in determining other information about an object that go beyond mere structural composition. For example, staining procedures can be used to determine information about the state of a cell's viability by selective staining with Syto dye and Propidium Iodide. The dominant fluorescence color of individual cells provides information about its viability.

The approaches described herein can obtain information about objects by receiving signals from them; for example, signals in the form of light can emanate from an object, whether through emission (e.g. radiation, fluorescence, incandescence, chemoluminescence, bioluminescence, other forms of luminescence, etc.), scattering (e.g. reflection, deflection, diffraction, refraction, etc.), or transmission, and can be sensed by a photodetector. Cells or other particles may be treated, e.g., stained or tagged with a suitable fluorescent probe or other agent, in such a way that they emit light or absorb light in a predictable fashion when illuminated with excitation light. In this regard, the light emitted by a given excited particle may be fluorescent in nature, or it may constitute a form of scattered light such as in the case of Raman scattering. For simplicity, the light that emanates from (by e.g., scattering, emission, or transmission) an object is referred to herein as "emanating light" or "light emanating." It will be understood that the techniques, assemblies, apparatuses, systems, and methods described herein are applicable to detecting all forms of light emanating from an object or constituent parts thereof.

The embodiments described herein relate to spatial distributions of one or more colors that may be present in light emanating from an object that has been spatially modulated by a spatial filter or mask. The spatially modulated light emanating from the object is sensed by one or more non-pixelated photodetectors which are particularly well-suited for high-throughput applications such as cytometry. Each of the photodetectors generates a time varying electrical signal in response to the sensed light.

It will be understood that the techniques, apparatuses, systems, and methods described herein are applicable to detect various objects present in a sample. The term "object" refers broadly to any object of interest to be detected. In some applications, objects of interest are particles or analytes that are relatively small, and may be microscopic in size. However, the techniques are broadly applicable to objects of any size or shape. A given particle or analyte may be or include one or a collection of biological cell(s), virus(es), molecule(s), certain proteins or protein chains, DNA or RNA fragments, molecular complex(es), droplets (e.g. oil in water), gas bubbles, microparticles, nanoparticles, beads or other small particles that can bind and carry specific chemicals.

Embodiments disclosed herein involve the spatial distribution of one or more colors of light emanating from objects. Emanating light of a particular color is associated with a characteristic wavelength spectrum of visible light, and may further extend into the non-visible range of wavelengths, including ultraviolet and infrared, for example. The characteristic spectrum of a color may be a relatively narrow wavelength, e.g., blue light is generally associated with a wavelength band from about 380 to 450 nm, red light is associated with a wavelength band from about 620 to 750 nm, and green light is associated with a wavelength band from about 495 to 560 nm. The color of light emanating from an object may be additive, meaning that the color of the emanating light can be a mixture of the wavelength spectra of other colors for example yellow light can be associated with a wavelength band from about 495 to 750 nm.

A property, such as a color of light emanating from an object, may have a spatial distribution meaning that an amount of a particular wavelength spectrum may vary with distance. In some scenarios, the emanating light may include a multiple colors, each color respectively associated with a wavelength spectrum, wherein each color can have a spatial distribution that varies or is uniform with distance. The distance can be the distance across the entire object or across one or more regions of the object. Different regions of the object may emanate differently colored light.

Figure 1B:
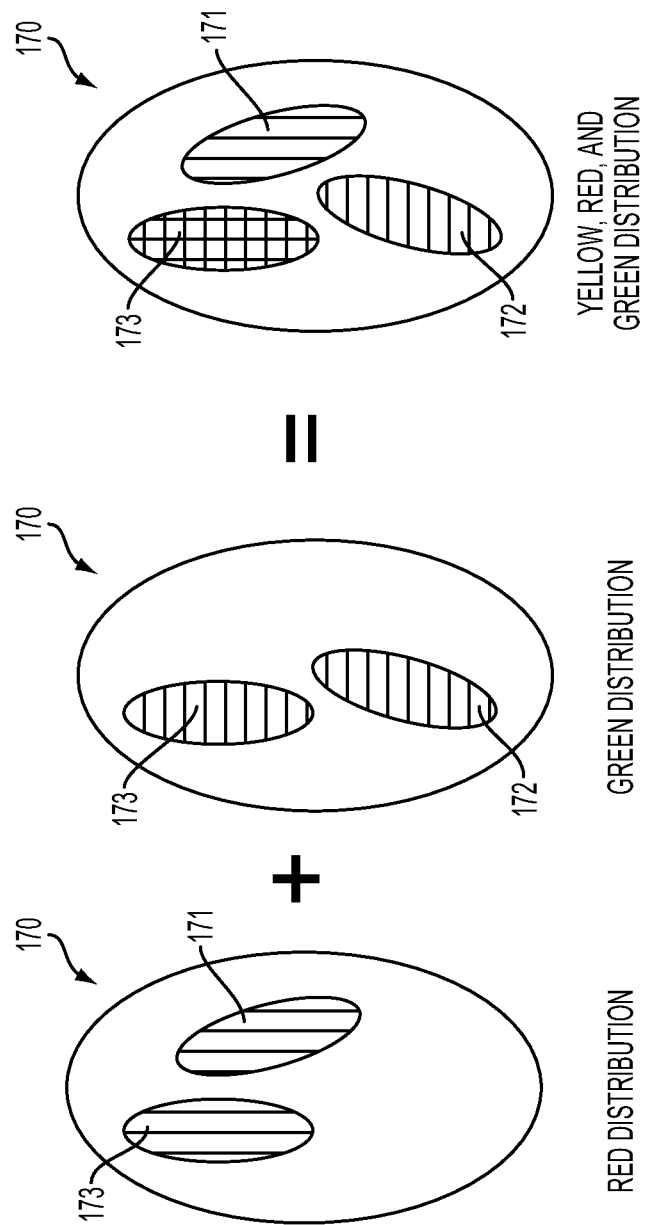

FIGS. 1A and 1B exemplify spatial distribution of color of light emanating from an object. FIG. 1A shows an object 160 that includes regions 161, 162, 163 that emanate light having a wavelength spectrum associated with a color "yellow" as indicated by cross-hatching of regions 161, 162, 163. The wavelength spectrum of color "yellow" includes the wavelength spectrum of color "red" (indicated by vertical crosshatching) and the wavelength spectrum of color "green" (indicated by horizontal crosshatching). The spatial distribution of the color red and the color green are substantially equal in regions 161, 162, 163 and colors red and green are referred to herein as being homogeneous in the object 161.

In contrast, FIG. 1B provides an example of inhomogeneous spatial distribution of color. FIG. 1B shows an object 170 that includes a region 173 that is yellow (red+green), region 171 that is red, and region 172 that is green. The spatial distribution of the color red does not substantially equal the spatial distribution of the color green and colors red and green are referred to herein as being inhomogeneous in the object 170.

In some implementations, the color spatial distribution of an object or region may be said to be substantially homogeneous with regard to colors "B" and "C" if the spatial distribution of color "B" varies by less than a predetermined amount as determined by the signals generated from light emanating from the objects or regions. An example of an inhomogenously colored object is a cell with cytoplasm stained a first color and a nucleus stained a different color. Some embodiments discussed herein involve determining whether the colors of emanating light have homogeneous or inhomogeneous spatial distributions.

Figure 1C:
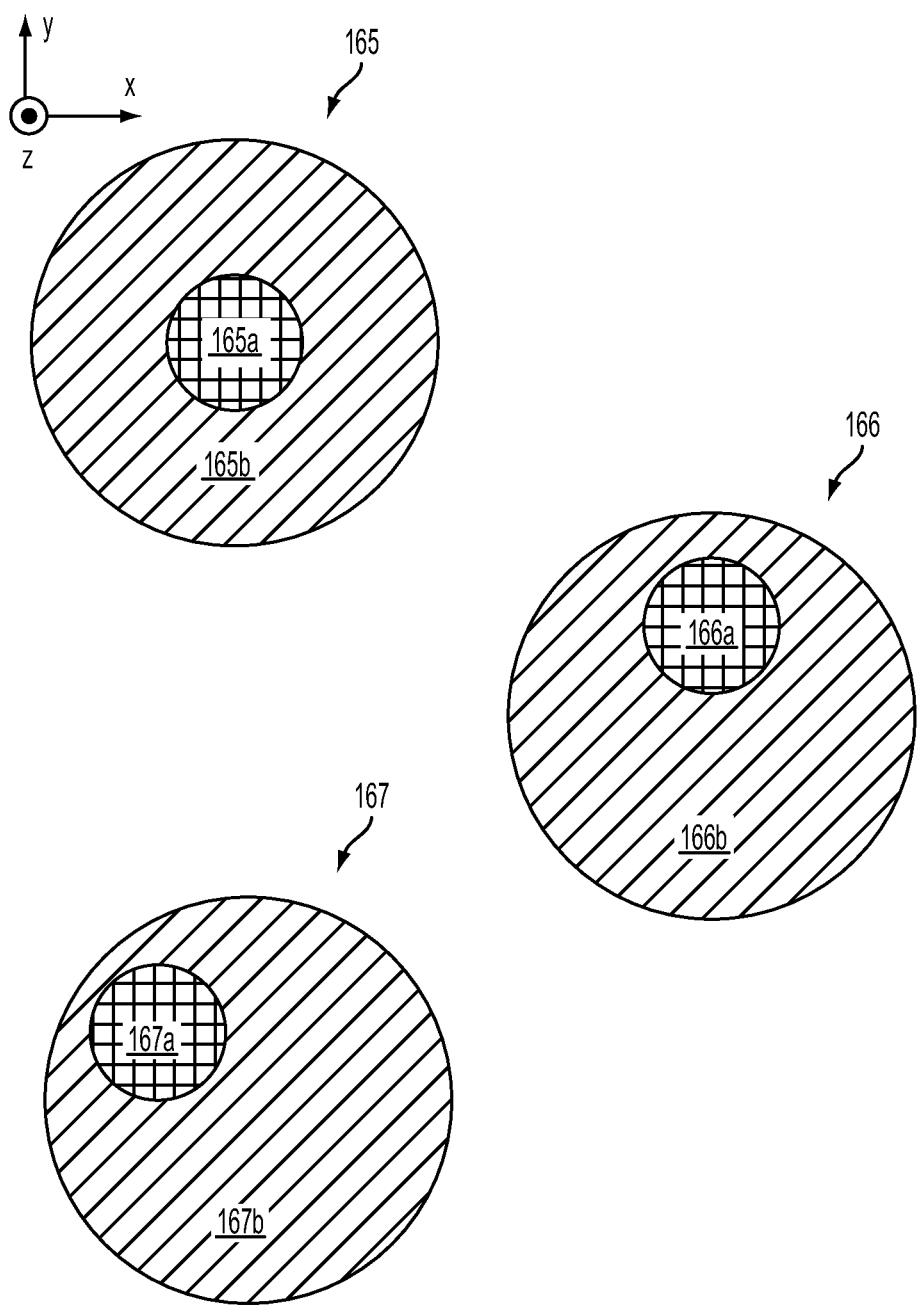
FIG. 1C depicts objects having symmetrical and asymmetrical color distributions.

Inhomogeneous color distributions can be symmetrical or asymmetrical with respect to an axis. For objects having symmetrical color distributions, it is possible to construct an axis spanning the object wherein the color distribution on one side of the axis is a mirror image of the color distribution on the other side. FIG. 1C illustrates object 165 having color regions 165a and 165b. The color regions 165a, 165b are symmetrically arranged with respect to the lateral axis (y-axis) and the longitudinal axis (x-axis) within color region 165b. Object 166 includes color region 166a surrounded by color region 166b. Color region 166a is arranged symmetrically with respect to the lateral axis (y-axis) and asymmetrically with respect to the longitudinal axis (x-axis) within color region 106b. Object 167 includes color region 167a surrounded by color region 167b. Color region 167a is arranged asymmetrically with respect to the lateral axis (y-axis) and asymmetrically with respect to the longitudinal axis (x-axis) within color region 167b.

Some embodiments employ two or more detectors, wherein a first detector is configured to detect light of a first color having a first wavelength range and a second detector is configured to detect light of a second color having a second wavelength range different from the first wavelength range. The wavelength ranges of the first and second colors may be a band of contiguous wavelengths or the wavelengths in the range may be non-contiguous.

Some embodiments can employ a single detector and a spatial filter that includes first and second mask features, wherein the first mask features have a first transmission characteristic and the second mask features have a second transmission characteristic different from the first transmission characteristic. For example, the first transmission characteristic can be selected to pass the wavelength range of a first color and the second transmission characteristic can be selected to pass the wavelength range of the second color.

Figure 1D:
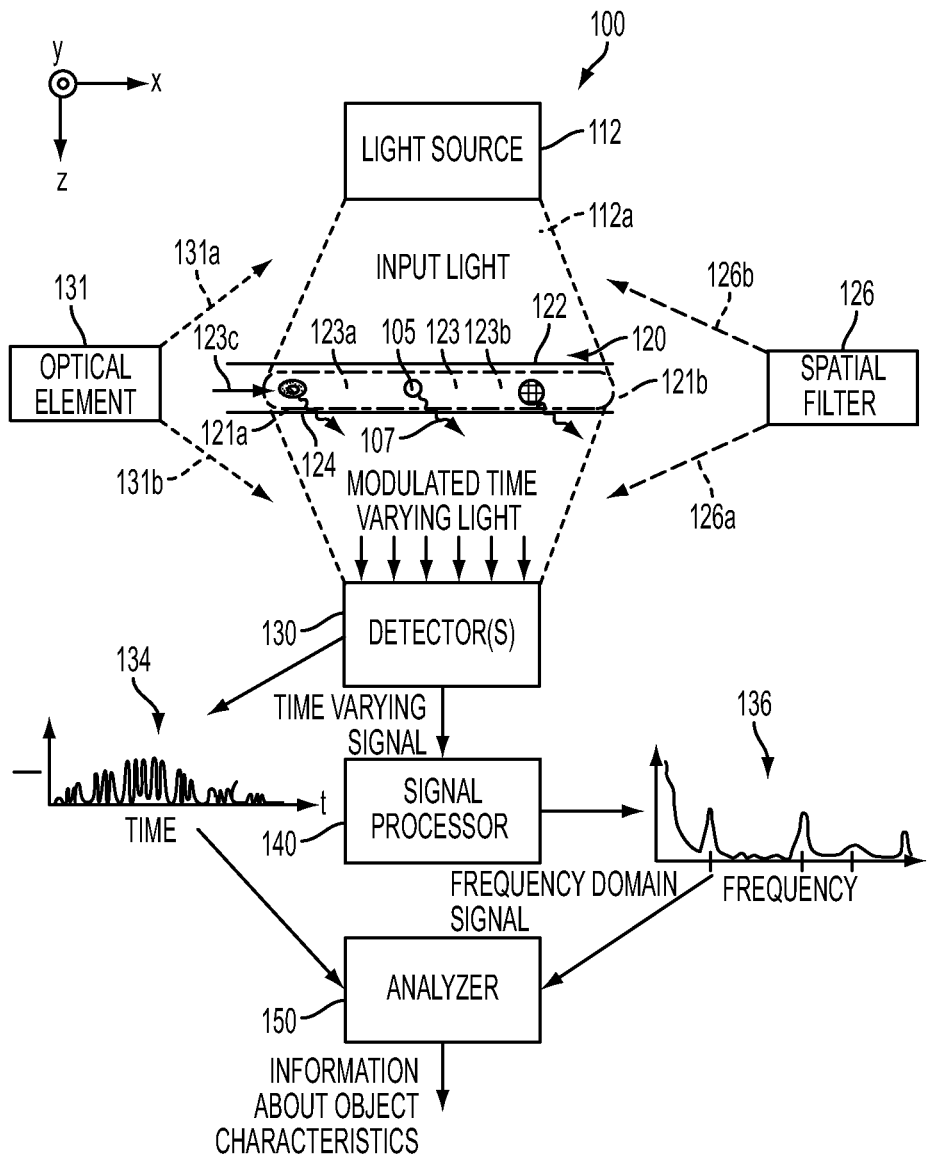
FIG. 1D is an example embodiment of a system configured to determine object characteristics based on spatially modulated light.

FIG. 1D is an example of an assembly 110 configured to determine object characteristics based on spatially modulated light. The assembly 110 includes a light source 112, a spatial filter 126, e.g. a mask, a flow path, e.g., fluidic device 120, a detector 130, a signal processor 140, and an analyzer 150. The fluidic device 120 is adapted to receive a sample of interest to be analyzed. The sample may enter the fluidic device 120 at an inlet 121a thereof and exit the fluidic device 120 at an outlet 121b thereof, flowing generally along the x-direction through a flow channel 123 formed between confining members 122, 124. The members 122, 124 may be or comprise plates or sheets of glass, plastic, or other suitable materials. One or both of members 122, 124 may be a microscope slide or a microscope cover glass, or portion thereof. The members 122, 124 need not, however, be planar in shape. For example, they may be portions of a unitary tube or pipe having a cross section that is circular, rectangular, or another shape. Other non-planar shapes are also contemplated. In some cases, confinement of the sample may not be necessary, whereupon one or both of members 122, 124 may be omitted. At least a portion of the confining member 122 is transmissive to excitation light emitted by the light source 112 at least in an excitation region 123a. In that regard, light source 112 may emit input light 112a towards the fluidic device 120.

In some cases, for example, the light source 112 may comprise a conventional light emitting diode (LED) source, a laser, a laser diode, a lamp or a resonant cavity LED (RC-LED) source. If desired, the light source may incorporate one or more filters to narrow or otherwise tailor the spectrum of the resultant output light. Whichever type of light source is selected, the spectral makeup or composition of the excitation light emitted by the source 112 is preferably tailored to excite, scatter, or otherwise cause emanation of light from at least some of the objects that may be present in the sample, as discussed further below.

The sample is depicted as containing exemplary objects 105 of varying color distributions as well as varying sizes and shapes. The objects 105 may emanate light 107 in all directions (only some directions are illustrated). The objects 105 may have a variety of characteristics, some of which can be determined by the analyzer 150 based on the emanating light 107. In some embodiments, one or more optical elements 131 such as a lens, an optical filter or dichroic mirror may be disposed in the path of the time varying light emanating from the objects and/or in the path of the input light. An optical element 131 may be disposed between the light source 112 and the flow channel 123, as indicated by dashed line 131a, and/or between the flow channel 123 and the detector 130, as indicated by dashed line 131b.

The detector 130 receives time varying light from the objects 105 as modulated by the spatial filter 126 and generates an electrical signal in response to the time varying light. The time variation in the light detected by the detector 130 may be the result of interaction between the excitation light and an input spatial filter to create spatially patterned excitation light that illuminates the object 105. Alternatively, the time variation in the light detected by the detector 130 may be the result of interaction between light emanating from the objects 105 and an output spatial filter. The time variation is based on the relative movement of the object 105 and the spatial filter 126.

In one embodiment, detector 130 is a sensing component that photosense a range of photon energies that emanate from objects. In some embodiments the sensing component can comprise a photosensor, which could, be a single, large area photosensor (such as a photodiode, an avalanche photodiode (APD), or a photo-multiplier tube (PMT)), or an appropriate array of photosensing cells whose sensed quantities can be combined to obtain a single photosensed quantity of spectral intensity over a sensing period.

The assembly 110 of FIG. 1D includes the spatial filter 126 (sometimes referred to as a mask) which can be positioned in various locations. Dashed arrows 126a and 126b indicate possible locations of the spatial filter 126 to provide spatially modulated light and/or modulated excitation light. In some configurations, indicated by arrow 126a, the spatial filter 126 can be disposed between the objects 105 and the detector 130. In this position, the spatial filter 126 is referred to as an output spatial mask. In other configurations, indicated by arrow 126b, the spatial filter 126 can be disposed between the light source 112 and the objects 105. In this position, the spatial filter 126 is referred to as an input spatial filter. An input spatial filter may be adapted to transmit light emitted by the light source by varying amounts along the excitation region 123a of the flow channel 123. In this configuration, the input spatial filter creates patterned excitation light in the excitation region 123a of the flow channel 123. According to various implementations, an input spatial filter may comprise a physical mask including a sequence or pattern of first regions that are more light transmissive and second regions that are less light transmissive. The input spatial filter may alternatively or additionally comprise optics, micro-optics or a patterned light source configured to create the excitation pattern. The excitation pattern can be imaged and/or directed onto the excitation region 123a using optical components for the imaging (e.g., lenses) and/or direction, (e.g., fiber optics or waveguides).

In some embodiments an output spatial filter may be utilized and disposed between the objects 105 and the detector 130 at a detection region 123b of the flow channel. In some embodiments, the excitation region 123a and the detection region 123b overlap. In other embodiments, there may be partial overlap between the excitation and detection regions or the excitation and detection regions may be non-overlapping or multiple detection regions and/or excitation regions may be used with various overlapping and/or non-overlapping arrangements. In the assembly 110 shown in FIG. 1, the output spatial filter may be adapted to interact with the light 107 emanating from the objects 105 in the flow channel 123. In some embodiments, the output spatial filter may be a physical mask comprising a sequence or pattern of first regions that are more light transmissive and second regions that are less light transmissive.

According to some embodiments of the assembly 110 that include the input spatial filter, as an object 105 travels in the flow direction 123c in the excitation region 123a of the flow channel 123, light emanating from the light source 112 is alternately substantially transmitted to the object 105 and substantially blocked or partially blocked from reaching the object 105 as the object 105 travels along the flow direction 123c. The alternate transmission and non-transmission (or reduced transmission) of the excitation light 112a along the flow direction 123c produces time-varying light 107 emanating from the object 105. The time-varying light 107 emanating from the object 105 falls on the detector 130 and, in response, the detector 130 generates a time-varying detector output signal 134.

According to some embodiments of the assembly 110 that include the output spatial filter configuration, light 112a from the light source 112 illuminates the object 105, causing the object 105 to emanate light 107. As the object 105 travels in the flow direction 123c in the detection region 123b of the flow channel 123, the output spatial filter alternatively entirely or substantially blocks the light 107 emanating from the object 105 from reaching the detector 130 and substantially transmits the light 107 emanating from the object 105 to the detector 130. The alternate substantial transmission and blocking (or partial blocking) of the light 107 emanating from the object 105 as the object 105 flows through the detection region 123b produces time varying light that falls on the detector 130. In response, the detector 130 generates the time-varying detector output signal 134.

In some embodiments such as the embodiment of FIG. 1D, the assembly 110 may include a signal processor 140 that converts the time-varying detector output signal 134 to a frequency domain output signal 136 so as to provide spectral power (e.g., the Fourier spectral amplitude) as a function of frequency. The signal processor 140 may be part of the detector 130 in some embodiments or may comprise separate circuitry in other embodiments. For example, in some embodiments, the signal processor 140 may be part of the analyzer 150 circuitry along with the detector 130. For conversion, the signal processor 140 may use known techniques such as, for example, a Fast Fourier Transform "FFT" algorithm. Thus, the frequency domain output signal 136 represents the frequency component magnitude of the time-varying detector output signal 134, where the frequency component magnitude is the amount of a given frequency component that is present in the time-varying detector output signal 134 or function. The Fourier signal power is a relevant parameter or measure because it corresponds to the function or value one would obtain by calculating in a straightforward manner the Fourier transform (e.g. using a Fast Fourier Transform "FFT" algorithm) of the time-varying signal 134. However, other methods or techniques of representing the frequency component magnitude, or other measures of the frequency component magnitude, may also be used. Examples may include e.g., the square root of the Fourier signal power, or the signal strength (as measured in voltage or current) obtained from a filter that receives as input the time-varying detector output signal 134.

In FIG. 1D, the time-varying detector output signal 134 and/or the frequency domain detector output signal 136 can be passed to the analyzer 150. The analyzer 150 receives the time-varying detector output signal 134, the frequency domain detector output signal 136, and/or any other processed signal from the detector. As will be discussed subsequently, the various embodiments discussed herein provide examples of techniques for determining the color distribution of the objects 105 using various mask designs and processing techniques. The color distribution determination can include various characteristics such as whether the object 105 is inhomogenously or homogenously colored, a location of the color, and an amount/size of a region of a particular color within the object 105. For example, size of a color region may be determined along the longitudinal axis (x-axis of FIG. 1D) parallel to the flow direction 123c, and/or size of a color region may be determined along the lateral axis (y-axis of FIG. 1D) perpendicular to the flow direction 123c, and/or size of a color region may be determined along the trajectory depth axis (z-axis of FIG. 1C).

Figure 2:
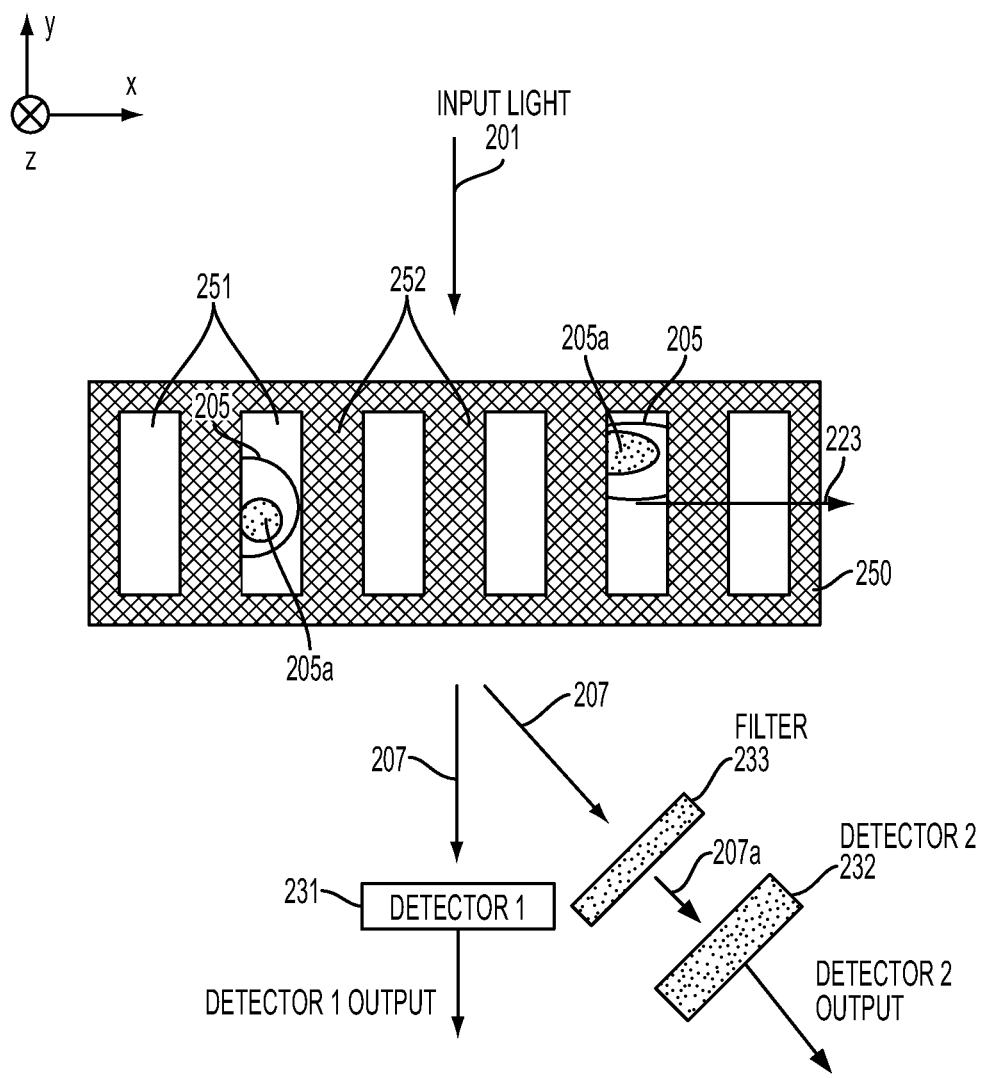
FIG. 2 is a diagram that conceptually illustrates a configuration for analyzing color distribution of objects that includes two detectors and an optical filter in accordance with some embodiments.

FIG. 2 conceptually illustrates a device configuration useful for determining color distribution according to some approaches. As illustrated in FIG. 2, objects 205 having an inhomogeneous color distribution are moving along a flow path 223 relative to spatial mask 250. The objects 205 encounter a number of transmissive 251 mask features interspersed with a number of opaque 252 mask features that are arranged longitudinally along the flow path 223. In some embodiments, the flow path 223 may be defined by confining members which are not shown in FIG. 2. As the objects 205 moves along the flow path 223, input light is scattered from the objects 205 and the input light excites at least a region 205a of the objects causing the region 205a to fluoresce.

The objects 205 may comprise one or more regions of different size and/or shape, and/or of different excitation region intensity and shape. As each object 205 moves along the flow path 223, over time the object will travel past each of the mask features 251, 252.

Light 207 emanating from object 205 is modulated by the transmissive and opaque features 251, 252 of spatial mask 250 and includes scattered light and fluorescent light. A first detector 231 detects the light 202 (both scattered and fluorescent) emanating from the object 250 and generates an electrical output signal in response to the sensed light.

An optical band pass filter 233 is arranged in the path of the emanating light 207. The band pass filter 233 blocks a portion of the emanating light and transmits a portion 207a of the emanating light to a second detector 232. For example, optical band pass filter 233 may be selected to substantially transmit wavelengths of the fluorescent component of the emanating light 207 in a certain band of wavelengths, and to substantially reject (block) other wavelengths. The second detector 232 senses the portion 207a of light transmitted by filter 233 and generates an electrical signal in response to the sensed light. A signal processor and/or analyzer (not shown in FIG. 2) can analyze the electrical signals generated by first 231 and second 232 detectors to determine the color distribution of the object 205.

Figure 3:
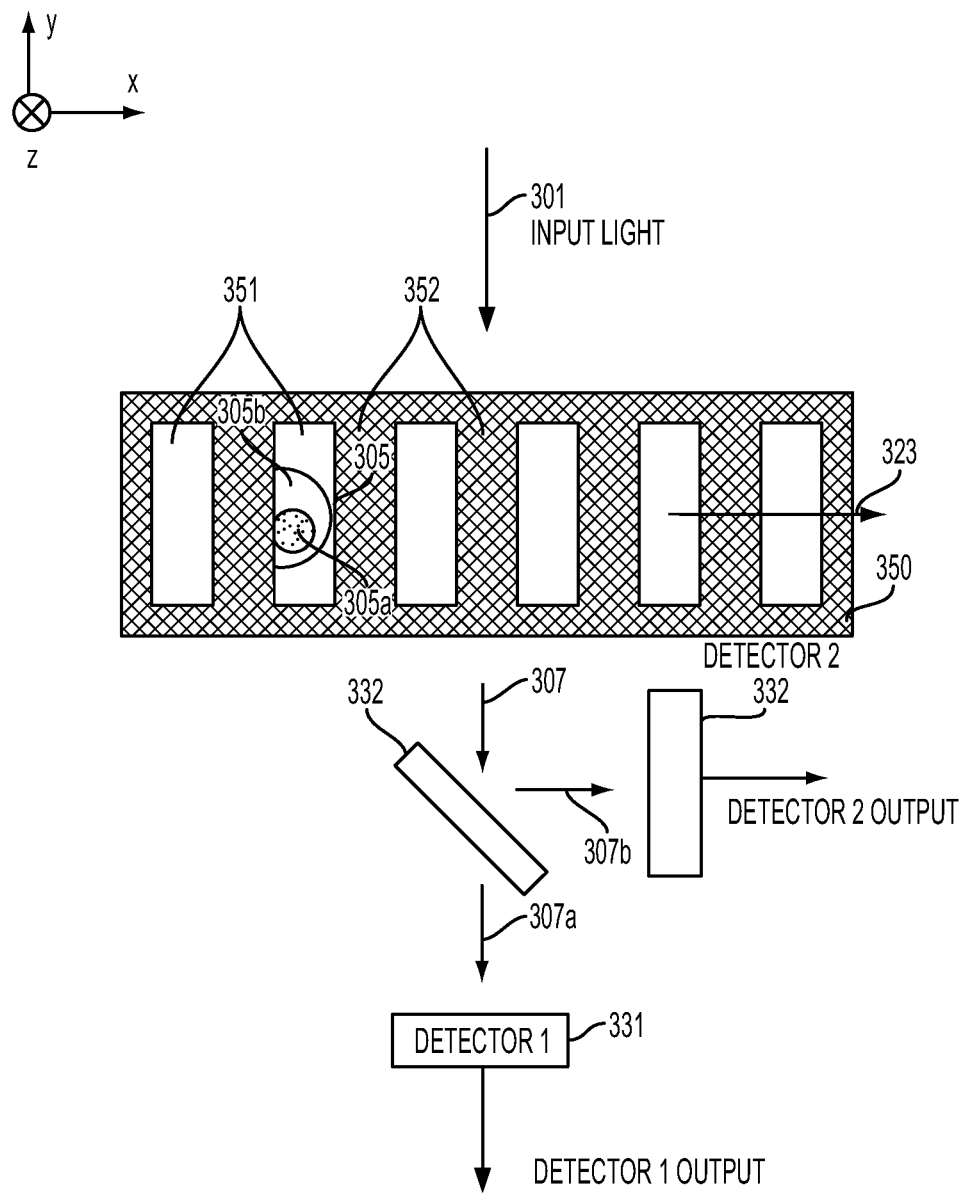
FIG. 3 is a diagram that conceptually illustrates a configuration for analyzing color distribution of an object that includes two detectors and two optical filters in accordance with some embodiments.

FIG. 3 conceptually illustrates a device configuration useful for determining color distribution according to some approaches. As shown in FIG. 3, an object 305 having an inhomogeneous color distribution is moving along a flow path 323 relative to spatial mask 350. As the object 305 moves along the flow path 323, the input light 301 excites first and second portions 305a, 305b of the object 305, causing regions 305a, 305b to fluoresce with different optical spectra. The light 307 emanating from object 305 includes the fluorescent light emitted from regions 305a and 305b. The device illustrated in FIG. 3 includes a dichroic mirror 332 that splits the emanating light 307 into first and second components 307a, 307b having differing optical spectra. The spectrum of the first portion 307a of light includes at least some of the wavelengths of the fluorescent light from region 305a. The spectrum of the second portion 307b of light includes at least some of the wavelengths of the fluorescent light from region 305b.

A first detector 331 is positioned to sense light 307a and generates an electrical signal in response to the sensed light 307a. A second detector 332 is positioned to sense light 307b and generates an electrical signal in response to the sensed light 307b. A signal processor and/or analyzer (not shown in FIG. 3) can analyze the electrical signals generated by first 331 and second detectors to 332 to determine the color distribution of the object 305.

FIGS. 2 and 3 illustrate configurations that can be used to determine color distribution of two colors of an object. However, it will be appreciated that additional optical filters and detectors and could be employed to sense additional components of light so as to determine color distribution of more than two colors of the object.

FIGS. 2 and 3 illustrate embodiments that include multiple color channels, wherein each color channel is configured to detect light in a different wavelength range than the other channels. Each of the color channels can be analyzed separately to determine one or more characteristics of an object or one or more regions of an object that emanate light that is detectable by the color channel. A number of systems, devices, and methods have been described for determining object dimensional characteristics and/or depth along a flow path using light emanating from objects wherein the emanating light is spatially modulated by spatial filters. Commonly owned U.S. patent application Ser. No. 14/181,560 describes determining depth of objects along a flow path based on spatially modulated light; commonly owned U.S. patent application Ser. No. 14/181,530 describes determining length of objects alon the flow direction of the flow path based on spatially modulated light; commonly owned U.S. patent application Ser. No. 14/181,525 describes determining width and/or thickness of objectsion based on spatially modulated light. Each of these patent applications are incorporated by reference herein.

In devices that include multiple color channels, a signal generated by the channel detector of a particular color channel includes information about the depth, length, width, and/or thickness of an object or a region within the object having the wavelength range detectable by the color channel. Thus, the spatial filters and applicable techniques described in each of the above referenced patent applications can be applied for each color channel in a system that includes multiple color channels to determine depth, width, length and/or thickness of the object or object region. Alternatively or additionally, signals from each of the color channels can be combined and/or compared to determine information about the color distribution of object regions as discussed herein.

Some embodiments involve the use of a color spatial filter that includes features that transmit light in different wavelength ranges. For example, a color spatial filter may include first features that transmit light in a first wavelength range and second features that transmit light in a second wavelength range. The color spatial filter may additionally include one or both of features that are substantially transmissive to both the first and second wavelength ranges and features that substantially block both the first and second wavelength ranges. In some implementations, light transmitted by the color spatial filters may be detected by a single detector which generates a signal that includes information about the depth, length, width, and/or thickness of objects of various colors and/or color regions within an object. Systems and methods described in U.S. patent application Ser. No. 14/181,560, U.S. patent application Ser. No. 14/181,530 and U.S. patent application Ser. No. 14/181,525, which are incorporated by reference herein may be used to analyze the detector signal.

Figure 4C:
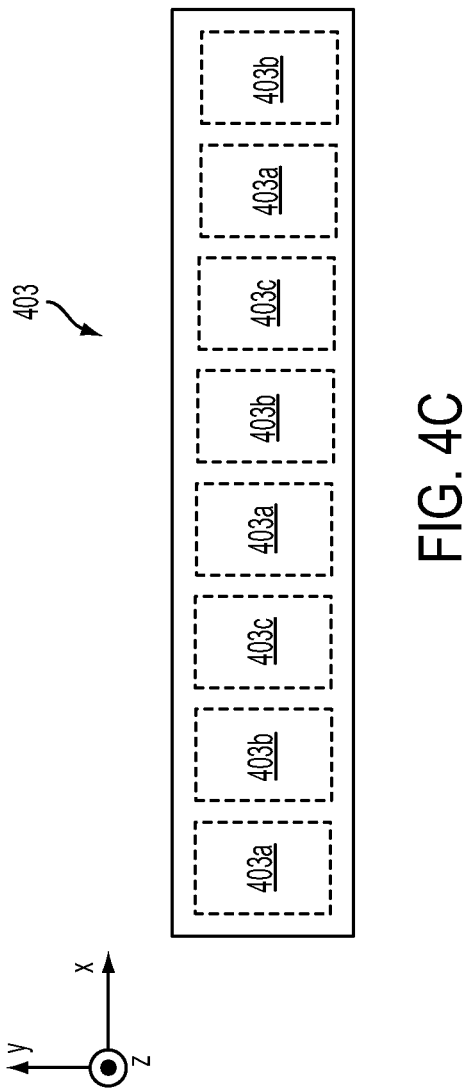

For example, in some implementations, the color mask features can be distributed in the spatial filter in several regions, as illustrated in FIGS. 4A-4C, wherein one or more first regions include features that are transmissive to a first wavelength range, one or more second regions include features that are transmissive to a second wavelength range, and one or more additional regions (if present) include features that are transmissive to additional wavelength ranges, etc. For example, spatial filter 401 of FIG. 4A shows two color regions 401a, 401b that are arranged along the longitudinal axis of the spatial filter 401; spatial filter 402 of FIG. 4B shows regions 402a, 402b arranged along the lateral axis of the spatial filter 402; and spatial filter 403 of FIG. 4C shows regions 403a, 403b, 403c interspersed along the longitudinal axis of the spatial filter 403.

FIG. 4A illustrates a spatial filter 401 having a first region 401a and a second region 401b that is arranged downstream along the flow direction (x-axis) from region 401a. As indicated in FIG. 4A, region 401a is located at x-axis position x1 and region 401b is located at downstream x-axis position x2. Color mask features having a first transmission characteristic may be arranged in region 401a and color mask features having a second transmission characteristic may be arranged in region 401b. Light emanating from objects that is modulated by the spatial filter 401 and is passed by the first or second transmission characteristics of the mask features in regions 401a or 401b includes information about characteristics of the objects. The characteristics may include dimensional characteristics, e.g., length, width, thickness, velocity, longitudinal, lateral, and depth position for objects and/or object regions.

FIG. 4B illustrates a spatial filter 402 having a first region 402a and second regions 402b, where region 402a is arranged between second regions 402b along the lateral y-axis. As indicated in FIG. 4B, region 402a is located at y-axis position y2 and regions 402b are located at y-axis positions y1 and y3. Color mask features having a first transmission characteristic may be arranged in region 402a and color mask features having a second transmission characteristic may be arranged in regions 402b. Light emanating from objects that is modulated by the spatial filter 402 and is passed by the first or second transmission characteristics of the mask features in regions 402a or 402b can be used to determine characteristics of the objects. Such characteristics may include dimensional characteristics, e.g., length, width, thickness, velocity, longitudinal, lateral, and depth position for objects and/or object regions.

FIG. 4C illustrates a spatial filter 403 having a first regions 403a, second regions 403b, and third regions 403c that are interspersed along the longitudinal axis (x-axis) of the spatial filter 403. Color mask features having a first transmission characteristic may be arranged in regions 403a, color mask features having a second transmission characteristic may be arranged in regions 403b, and color mask features having a third transmission characteristic may be arranged in regions 403c. Light emanating from objects that is modulated by the spatial filter 403 and is passed by the first, second or third transmission characteristics of the mask features in regions 403a, 403b, 403c can be used to determine characteristics of the objects. Such characteristics may include dimensional characteristics, e.g., length, width, thickness, velocity, longitudinal, lateral, and depth position for objects and/or object regions.

Figure 4D:
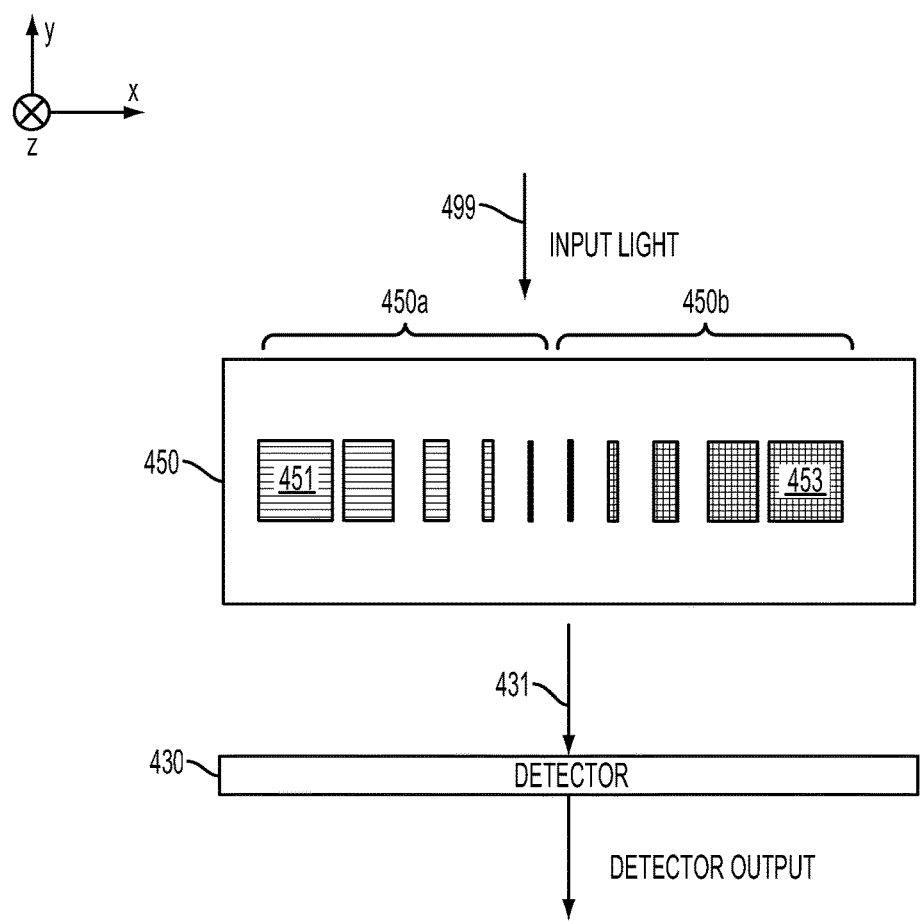
FIG. 4D shows a color spatial filter that can be used with a single detector for determining lengths for color objects or color regions within an object.

FIG. 4D conceptually illustrates a device configuration that includes a color spatial filter 450 that includes first and second regions 450a, 450b arranged as illustrated generally in FIG. 4A. The color features of the spatial filter 450 are arranged so that they are particularly useful for determining length of an object or regions within an object that emanate light that is passed by the transmission characteristic of the first 451 or second 453 mask features.

Mask 450 includes a first mask region 450a having first features 451 configured to transmit a first wavelength range of light and a second mask region 450b having second features 453 configured to transmit a second wavelength range. The first and second features 451, 453 may be interspersed with opaque features as shown in FIG. 4D.

In this example, the detector output signal from detector 430 includes information about the length of objects of either a first or second color (or object regions of either the first or second color) where each color is transmitted by one or the first features 451 or the second features 453. The signal from the detector is time multiplexed with respect to the first and second wavelength range transmitted by the spatial filter as discussed below. The length of an object or object region of the first color and/or the length of the object or object region of the second color can be determined, for example, using the technique described in commonly owned U.S. patent application Ser. No. 14/181,530 which is incorporated by reference herein.

An inhomogeneously colored object (such as object 305 shown in FIG. 3) includes first and second regions 305a, 305b that can be excited by input light 401 causing the regions 305a, 305b to emit fluorescent light. For example, region 305a may emit fluorescent light having a first spectrum associated with a first color and region 305b may emit fluorescent light having a second spectrum associated with a second color. The first spectral range transmitted by the first features 451 is selected to pass at least some of the wavelengths of the fluorescent light emitted by the first region 305a of the object 305. The second spectral range of the second features 453 is selected to pass at least some of the wavelengths of the fluorescent light emitted by the second region 305b of the object 305. As the object moves past the first features 451, information about the size of the first region 305a is included in the emanating light 402a. As the object moves past the second features 453, information about the size of the second region 305b is included in the emanating light 402b. The detector 430 senses the light 402a, 402b time modulated by the first features 451 and the second features 453 and generates a time varying electrical signal. A signal processor and/or analyzer (not shown in FIG. 4D) can analyze the electrical signal generated by the detector to 430 to determine the color distribution of the object 305. FIG. 4D illustrates a configuration that can be used to determine color distribution of two colors of an object. However, it will be appreciated that third, fourth or more mask regions having third, fourth or more mask features configured to pass third, fourth, or more spectral ranges could be employed determine color distribution of more than two colors of the object.

Figure 4E:
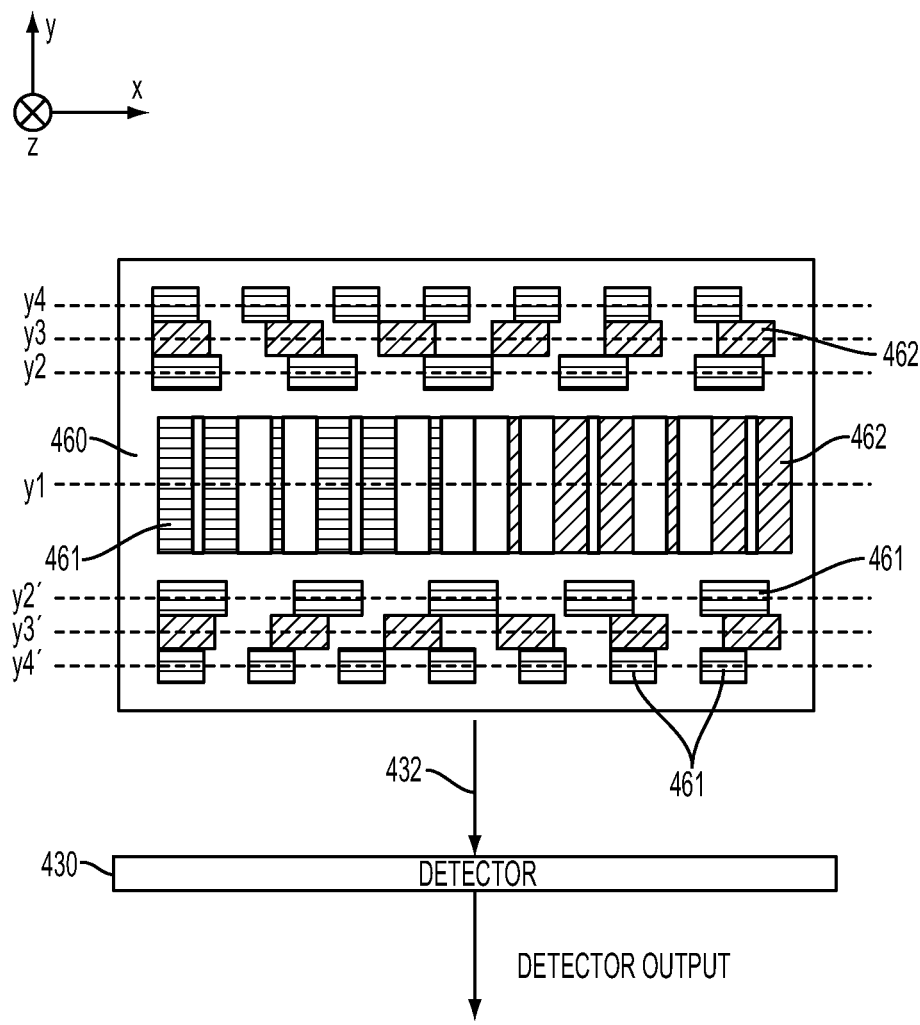
FIG. 4E shows a color spatial filter that can be used with a single detector for determining widths or thicknesses for color objects or color regions within an object.

FIG. 4E shows a device useful for determining length and width (or thickness) of color objects or color regions within an object using a color spatial filter. Color spatial filter 460 includes first mask features 461 (horizontal shading) having a first transmission characteristic associated with a first color and second mask features 462 (angled shading) having a second transmission characteristic associated with a second color. Features 461 and 462 are arranged along the longitudinal x-axis of the spatial filter 460 at lateral position y1. The pattern at lateral position y1 is a two frequency arrangement with frequency fm2 superimposed on frequency fm1 along the x-axis for both of the colors (features 461 for detecting the length of objects or regions having a first color are arranged on the left and features 462 for detecting length of objects or regions having a second color are arranged on the right of the spatial filter in FIG. 4E. Features 461 are arranged along lateral positions y2 and y2' in a pattern having a frequency f2 along the x-axis Features 462 are arranged along lateral positions y3 and y3' in a pattern having frequency f3 along the x-axis. Features 461 are arranged along lateral positions y4 and y4' in a pattern having frequency f4 along the x-axis wherein f2<f3<f4<fm1<fm2 in this example, although other frequency relationships could be used. The light emanating from color objects or color regions with in objects that is transmitted by features 461 or 462 includes information about the length and width (or thickness depending on the orientation of the spatial filter 460) of the objects or object regions. Determination of length and width of objects can also be applied to determining length and width of color objects or color regions of objects and is further discussed in U.S. patent application Ser. No. 14/181,525, which is incorporated by reference herein.

For device configurations similar to those shown in FIGS. 2 through 4E, the one, two (or more) time varying signals generated in response to sensed light can be used in several ways to determine various object characteristics including color distribution. The techniques as described in U.S. Pat. No. 7,358,476 (Kiesel et al.), entitled "Sensing Photons from Objects in Channels" and U.S. Pat. No. 8,629,981 (Martini et al.), entitled "Analyzers with Time Variation Based on Color-Coded Spatial Modulation", the disclosures of which are incorporated herein by reference in their entireties, can be used to determine characteristics of the objects. For example, the objects speed and the length of the corresponding time dependent fluorescence intensity trace (time varying electrical signal) can be calculated for the object. For each time varying electrical signal, the correlation integral of the fluorescence signal with the known mask function can be calculated. The value of these correlation integrals corresponds to the relative brightness of fluorescence for each of the at least two time varying electrical signals. The simultaneous sections of the at least two time varying electrical signals now contain the fluorescence information of an identical particle and can be compared. Additionally, the transmission characteristics and geometry of the mask features of the spatial filter are known and may serve as supplementary reference points for the emanating light signal converted to an electrical signal by the detector.

The approaches discussed in U.S. patent application Ser. No. 14/181,560, U.S. patent application Ser. No. 14/181,530 and U.S. patent application Ser. No. 14/181,525 which are incorporated by reference can be modified according to the configurations illustrated in FIGS. 4A-4E to utilize color mask features and may be used to determine characteristics of colored objects or of characteristics of colored regions within objects including color distribution of the color regions.

FIGS. 5A to 5D show one technique that allows a color distribution to be determined by subtracting, for each point in time, the amplitude of the first time varying electrical signal generated by the first detector from the corresponding amplitude of the second time varying electrical signal generated by the second detector. In some implementations, the two or more time varying electrical signals can be normalized by their respective correlation integral value and then subtracted from each other. The resulting time series should be zero (or close to zero) for each data point, if the color distribution is homogeneous. Other scaling operations for each signal may result in the similar results.

Figure 5A:
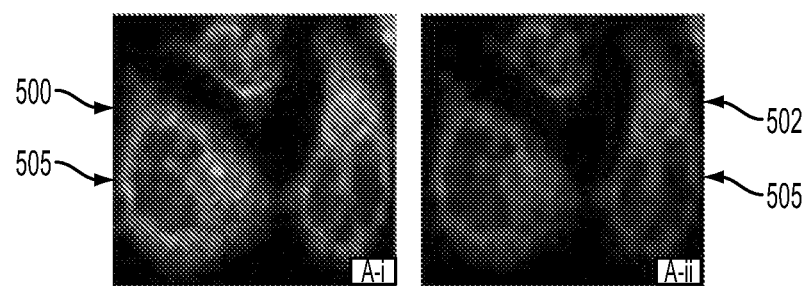
FIG. 5A shows two images of homogeneously colored objects, one of the images shows light emanating from objects in a first wavelength range and the second image shows light emanating from the same objects in a second wavelength range.
Figure 5B:
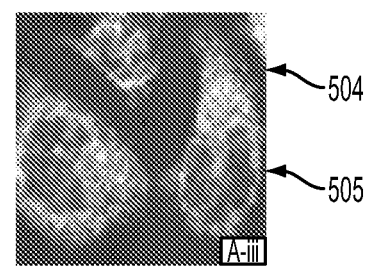
FIG. 5B is a third image of the homogeneously colored objects from FIG. 5A in a combined wavelength range that includes both the first wavelength range and the second wavelength range.

FIG. 5A shows two images 500 and 502 of homogenously colored objects 505. The first image 500 illustrates light emanating from objects 505 in a first spectral range while the second image 502 illustrates light emanating from the objects 505 in a second spectral range. FIG. 5B shows a third image 504 of the homogenously colored objects in a combined spectrum that includes both the first spectral range and the second spectral range.

Figure 5C:
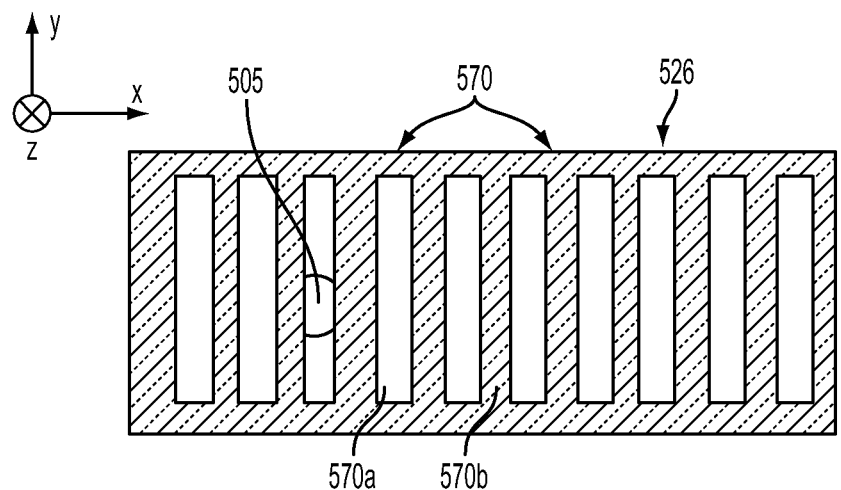
FIG. 5C a plan view of a spatial filter having periodically arranged mask features.

FIG. 5C shows a plan view of a spatial filter 526 with one of the objects 505 disposed adjacent thereto. Object 505 has light emanating therefrom that is time modulated by the mask features 570 including more light transmissive features 570a and less light transmissive features 570b.

Figure 5D:
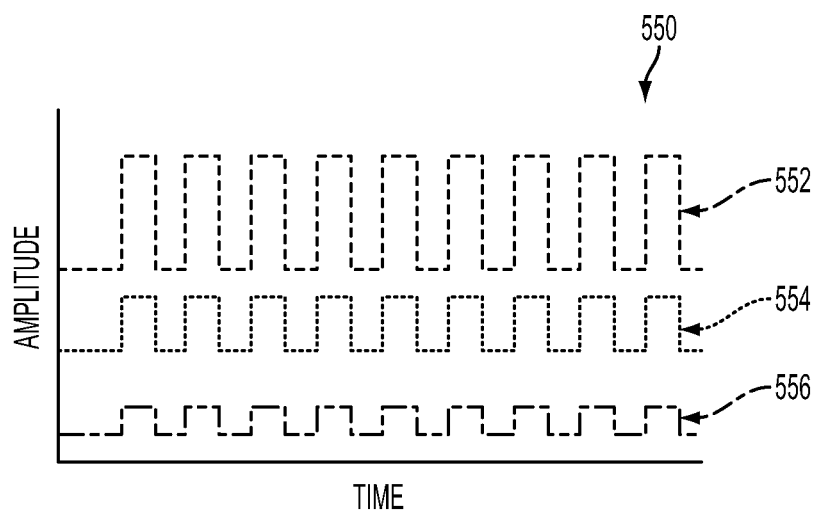
FIG. 5D are simplified plots of a first output signal from a first detector generated in response to light in a first wavelength range, a second output signal from a second detector generated in response to light in a second wavelength range, and a difference signal between the first and second output signals.

FIG. 5D shows a simplified plot 550 of first and second output signals 552 and 554 that result from light modulated by the spatial filter 526 of FIG. 5C and segregated into a particular spectral ranges falling on two or more detectors (not shown). In FIG. 5D, output signal 552 corresponds generally to the intensity of light sensed in the first spectral range (image 500 of FIG. 5A). Similarly, output signal 554 corresponds generally to the intensity of light sensed in the second spectral range (image 502). The signal 556 is the difference of the output signals 552 and 554. In some embodiments, the analyzer includes a differential amplifier configured to determine the difference between the output signals 552, 554 and to output the difference signal 556. It should be appreciated that the signals 552, 554 and 556, in FIG. 5D are shown shifted in the vertical direction as to separately show each signal relative to each other. In practice, the signals 552, 554, 556 may be partially overlapping in the vertical direction.

In the embodiment of FIG. 5D, the signals 552, 554, and 556 include characteristics (such as changes in at least one of amplitude and/or a frequency) that are directly associated with the mask features 570 and the color distribution within the object. In particular, the amplitude of the signals 552, 554, and 556 rises in a closely timed and directly correlated manner due to more light transmissive regions 570a and falls in a closely timed and directly correlated manner due to less light transmissive regions 570b. In some embodiments, the mask features 570 can be configured with a simple periodic pattern. This simple periodic pattern, when reflected in the signals 552, and 554 can be a characteristic directly associated with the mask features 570.

The analyzer (not shown) can be configured to determine the color distribution, including an amount of color homogeneity or inhomogeneity of the object 505 (FIG. 5A) based upon the characteristics of the signals 556.

The analyzer can determine that the object 505 has a homogenous color distribution if the first and second signals have a combined signal (signal 556) of the first signal 552 and the second signal 554 has one or more characteristics directly associated with the mask features 570. In one embodiment, the analyzer can determine if the object 505 has a homogenous color distribution if a difference between the first signal 552 and the second signal 554 has a periodic pattern that corresponds to the periodicity of the mask features. In that case a substantially homogeneously stained object has passed by the periodically patterned mask. If the coloring of an object is inhomogeneous, signals generated by different color regions of the same object would vary in one or more of frequency, phase, and duty cycle (pulse width). For example, in the concentric region example discussed below, the smaller region would produce a signal having a different duty cycle than the signal produced by the larger region, but the frequency of the signal would be the same. The difference signal would have a higher frequency component than the frequency component of the mask features.

Figure 5E:
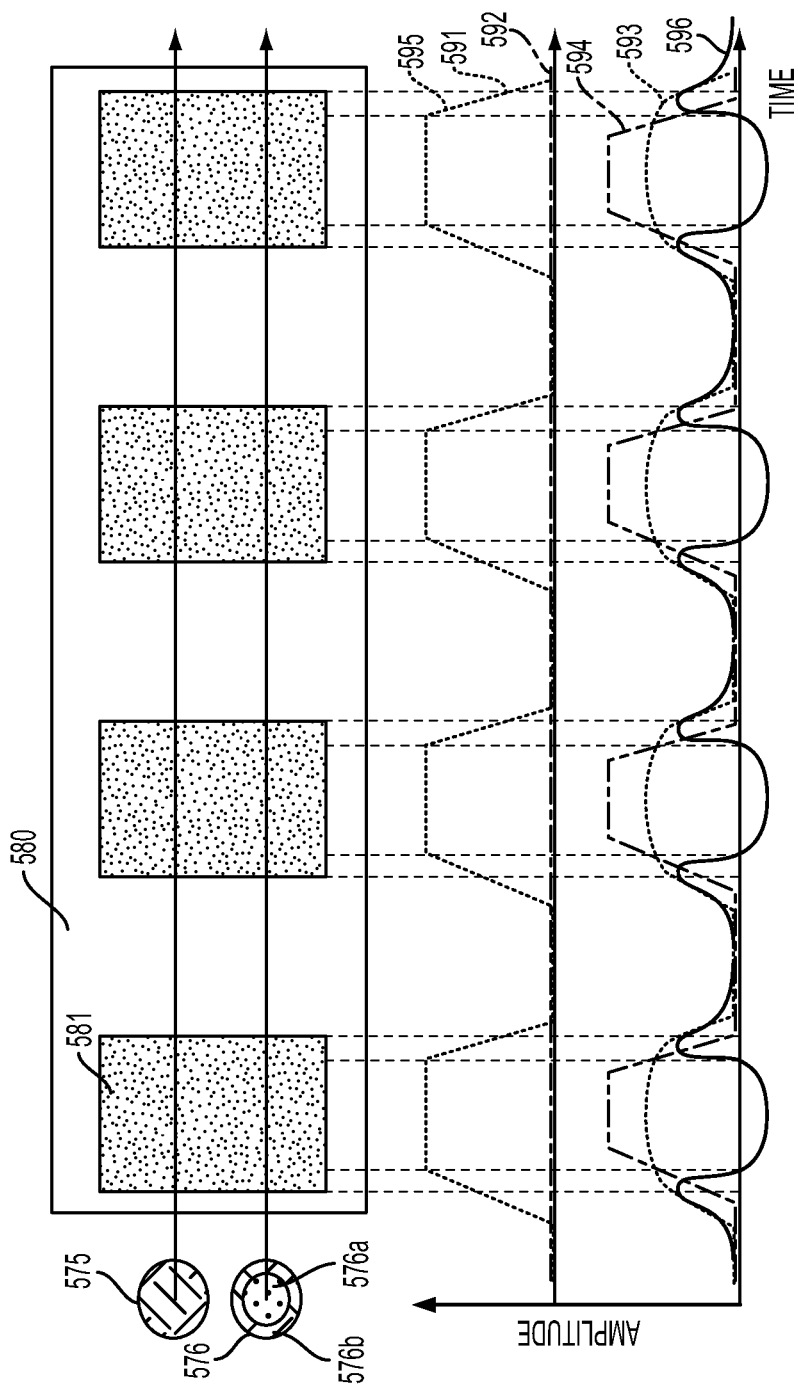
FIG. 5E illustrates a process of determining color characteristics of objects.

FIG. 5E is an example showing two object types 575, 576 passing by periodically arranged mask features 581 of a spatial filter 580. Object 575 has a uniform color distribution (arbitrarily referred to as "red"), matched to the first detector, and object 576 has the same color as object 575 in the outer region 576b, and a second color (arbitrarily referred to as "green") in the smaller center region 576a. The objects 575, 576 are observed with two detectors, the first detector is used with a first filter that transmits red to the first detector and substantially block greens, while the second the detector is used with a second filter configured to transmit green to the second detector and to substantially block red. The first and second detector outputs are shown as plots 591-594.

Approximated detector outputs for the object 575 are shown in the upper plots 591, 592. The approximated plots 591-594 (and other graphs/plots herein) are shown as conceptual, approximated plots and straight lines are used instead of rounded lines (which would likely be present in actual plots due to the round object shapes). Since the top object 575 emits no green light component, the output from the second detector is zero. The output from the first detector (plot 591) is influenced only by the red light component which is modulated by the periodic mask features 581. The difference 595 between the first 591 and second 592 detector outputs is the same as the first detector output plot 591 because the second detector output plot 592 is zero for object 575.

The bottom object 576, however, has both red 576b and green 576a regions. The output plots from the first 593 and second 594 detectors are shown in the bottom graph. The duty cycle of the positive going pulses of the first detector output plot 583 is greater than the duty cycle of the positive going pulses of the second detector output plot 594 (i.e., each positive going pulse starts earlier and ends later) for each more transmissive mask feature 581, since the outer region 576b is wider than the center region 576a. After the initial rise, the first detector signal 593 continues to grow slowly as more of the outer region 576b becomes visible through the mask feature 581. The second detector signal 594 for object 576 has a shape that is similar in some respects to the first detector signal for object 575 (the center region 576a being a single-colored circle). However, the duty cycle of the positive going pulses of the first detector output signal 591 is greater than the duty cycle of the positive going pulses of the second detector output signal 594 because the diameter of center circle region 576a is smaller than circular object 575.

The analyzer can determine that the object 575 is homogeneous by taking the difference between first 591 and second 592 detector signals, for example. The difference signal 595 for object 575 is the same as the first detector output signal 591 (since the second detector output signal 592 is zero everywhere), and the pattern of the difference signal 595 directly corresponds to the periodic mask modulation.

The shape of the difference signal 596 for the object 576 significantly deviates from the periodicity of the mask features. When the object 576 is at the outer edges of the more-transmissive mask features 581, the first detector signal 593 rises first while the second detector signal 594 is still low, leading to a positive increase in the difference signal 596. When the second detector signal 594 begins to increase, the difference signal 596 begins decreasing. When the object 576 is at the center of the more-transmissive mask features 581, the second detector signal 594 is larger than the first detector signal 593, resulting in a lower difference signal 596. At the points where the first detector signal 593 equals the second detector signal 594, the difference signal 596 is zero. When the second detector signal 594 becomes larger than the first detector signal 593, the difference signal 596 becomes negative.

The analyzer can be configured to analyze the shape of the first detector output signal 593, the second detector output signal 594, and/or the difference signal 596 (or other combination of the first and second output signals) that the object 576 is inhomogeneously colored "red" on the outer edges and "more green than red" at the center.

Note in addition that even if the top object in FIG. 5E was homogeneously colored with a mixture of both red and green, both red green output signals would be similar, just with different amplitudes, and the difference signal would also have the same shape and mask periodicity (since both signals are of the same width).

Figure 6A:
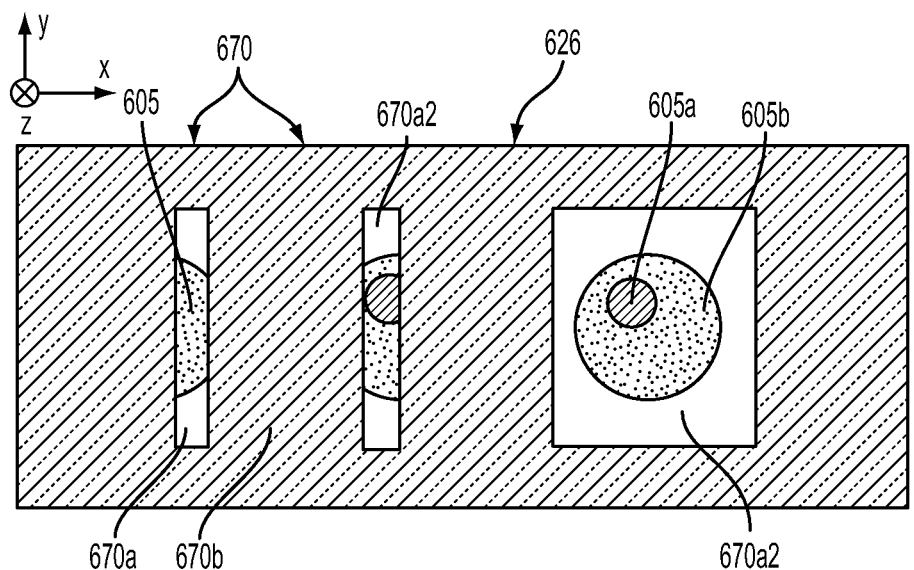
FIG. 6A is a plan view of a spatial filter with and an object having an inhomogeneous and asymmetrical color distribution moving relative to the spatial filter.

FIG. 6A shows a portion of a spatial filter 626 with an object 605 moving with respect to the spatial filter. In FIG. 6A, the object 605 is inhomogeneously colored and the color regions 605a, 605b are asymmetrical with respect to the x and y axes. Object 605 includes a larger region 605b that emits light in a first spectral range and a smaller region 605a that emits light in a second spectral range. As the object 605 travels relative to the spatial filter 626, light emanating from the object 605 is modulated by the mask features 670 including the more light transmissive features 670a and the less light transmissive features 670b.

Figure 6B:
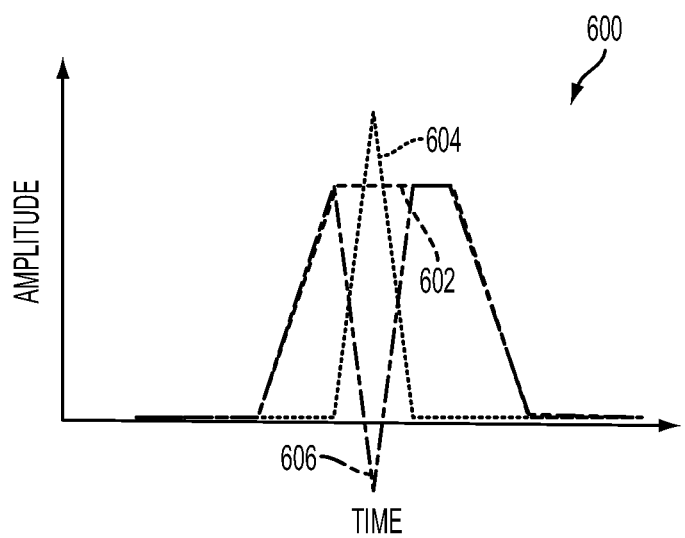
FIG. 6B is a simplified plot of a first output signal generated by a first detector in response to light in a first wavelength range emanating from the object shown in FIG. 6A, a second output signal generated by a second detector in response to light in a second wavelength range emanating from the object shown in FIG. 6A, and a difference signal between the first and second output signals.

In configurations as illustrated by FIGS. 1, 2 and/or 3, light in the first spectral range emitted by the region 605b is sensed by a first detector and the first detector generates a time varying electrical output signal 602 in response to the sensed light. Light in the second spectral range emitted by the region 605a is sensed by the second detector and the second detector generates a time varying electrical output signal 604 in response to the sensed light. FIG. 6B shows an plot 600 of first and second approximated output signals 602 and 604 generated by first and second detectors, respectively, as the object 605 passes by mask feature 670a2. In FIG. 6B, the first output signal 602 corresponds generally to the intensity of light emitted from larger region 605b and the second output signal 604 corresponds generally to the intensity of light emitted from smaller region 605a. The signal 606 is a combined signal representing the difference between the amplitude of the first time varying electrical output signal 602 and the second time varying electrical output signal 604.

Signal 606 includes characteristics (such as changes in at least one of amplitude and/or frequency) that are not directly associated with the mask features 670. The amplitude of the signals 602, 604, and 606 rise and fall at different rates and at different points in time. The rise and fall of the amplitude of signal 606 is not closely timed and simply correlated with regard to more light transmissive regions 670a and less light transmissive regions 670b. In some embodiments, the mask features can be arranged in a single frequency periodic pattern, as shown by mask 250 of FIG. 2.

In FIG. 6B, the basic fundamental frequency (the strongest component) of the difference signal 606 is still driven by the mask. For a small object region size relative to the mask opening, ignoring the small rise and fall times, the output signal for a uniform (homogeneous) color object would approximate a square wave comprising the basic frequency of the mask and harmonic multiples thereof in the frequency domain. The magnitude and frequency of each harmonic can be determined from the signal waveform.

In the case of an inhomogeneous object, the difference between the signal outputs for the color regions creates additional frequency components, beyond those predicted by the square wave shape of a homogeneous object or object region. These additional frequencies can be identified by the analyzer using frequency domain analysis. Alternatively or additionally, using time domain analysis, the inhomogeneity of an object can be detected when there are deviations from the predictable square wave output, as illustrated by the shape of the difference signal 606. Inhomogeneously colored objects can be identified by observable deviations from the predictable mask modulation patterns of homogeneously colored objects in the time domain. Alternatively or additionally, inhomogeneously colored objects can be identified in the frequency domain by the presence of additional frequency components beyond the fundamental mask frequency and its corresponding harmonics produced by homogeneously colored objects.

Based upon the techniques described, an analyzer can be configured to determine that the object 605 has an inhomogeneous color distribution when the combined signal 606 of the first signal 602 and the second signal 604 does not have one or more signal characteristics directly associated with the mask features 670. In particular, the analyzer can determine the object 605 has an inhomogeneous color distribution if a difference between the first signal 602 and the second signal 604 does not reproduce the mask pattern in a similar manner as do the individual detector signals 602 and 604.

Cross-correlation is another technique that can be performed on the two or more time varying electrical signals to determine whether color distribution within the object is homogeneous or inhomogeneous. This cross correlation could also be normalized by the initial correlation integral values or by the cross correlation values of the individual time varying signals with the mask function. Higher values of the cross-correlation value will indicate homogeneous color distributions.

With reference to the example shown in FIG. 5E, and assume the first and second object color regions are known in advance (for example "red" and "green"). In many practical situations these colors are determined by the choice of inks or fluorescent dyes/tags or stains used, and/or by the optical characteristics of the reflective/absorptive coating applied, etc. Assume further that a first and a second detector are selected to substantially detect one color and substantially block the other color. Unknown objects, which may or may not be homogeneous in color, are traveling in front of the mask.

If an object is homogeneous in color e.g., object 575, the first and second detector outputs would look like the graphs 591 and 592 in FIG. 5E, and the difference signal 595 is the same as the graph 591 since graph 592 is zero everywhere.

For an unknown object, the cross correlation technique would attempt to cross correlate the unknown object (difference) signal with the predicted curve 595 of a homogeneous object. If the unknown object happens to be homogeneous, the difference signal will essentially be cross-correlated with itself leading to a large value, e.g., the largest possible value for the cross-correlation.

If, on the other hand, the object happens to be inhomogeneous, as in the case of the bottom object 576, the difference signal 596 will be cross correlated with the expected curve 595 resulting in a much lower cross-correlation value than for a homogeneous object, due to the signal mismatch.

The analyzer can therefore determine that an object is or is not homogeneous based on the cross correlation value. Only signals from homogeneous objects would approach the predicted cross correlation value.

The approach disclosed herein includes setting up an appropriate threshold for the analyzer to identify when an object is homogeneously colored based on the cross correlation value. Methods involve normalizing the cross correlation integral value, either with respect to the actual measurements of the signals from known objects (a.k.a. calibration), and/or by generating noisy signals using simulation and cross-correlating them with the predicted mask signals, and/or by measuring or simulating signals of sufficiently inhomogeneous objects and setting the threshold value based on signal obtained from the inhomogeneous objects. Any one of the above methods or in combination of the methods may be used. The normalization allows for the use of a fixed cross correlation threshold.

Color regions may be arranged within objects asymmetrically or symmetrically. Objects having asymmetrical arrangements of color regions have inhomogeneous color distribution. In some embodiments, the derivatives of the time varying signals for the color regions can be used to determine whether the color regions within objects are arranged symmetrically or asymmetrically with respect to each other.

Figure 7A:
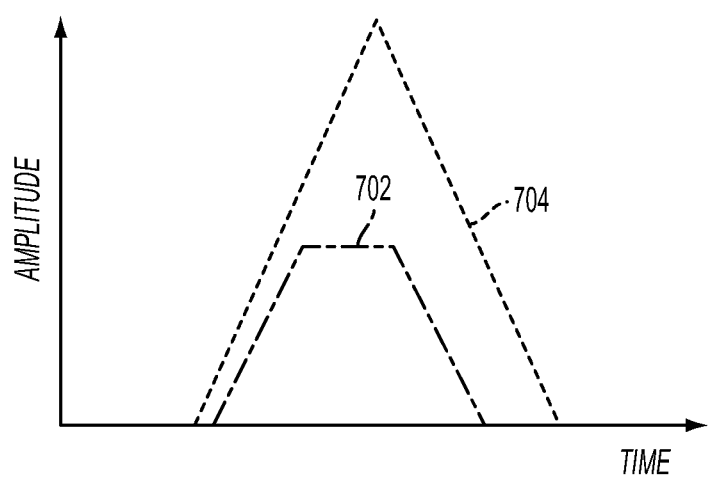
FIG. 7A depicts graphs of approximated first time varying signal and second time varying signal generated in response to sensing light modulated by a light transmissive.
Figure 7B:
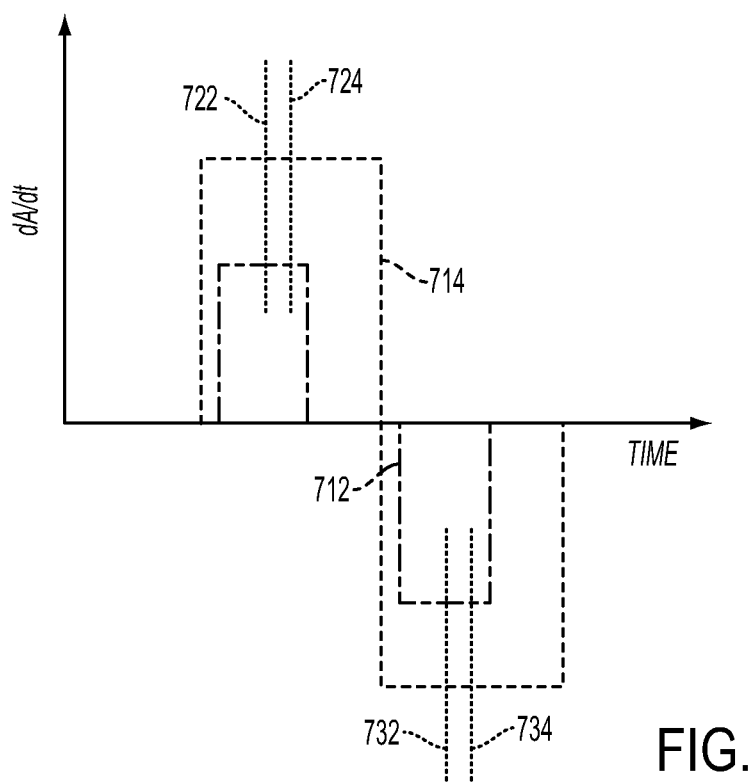
FIG. 7B shows plots of the derivative of the approximated first time varying signal and second time varying signal from FIG. 7A.

FIG. 7A illustrates time varying signals 702, 704 generated by first and second detectors in response to emanating light from an object that is inhomogeneously colored and that has color regions that are asymmetrically arranged. FIG. 7B shows plots 712, 714 of the amplitude derivative of the first time varying signal 702 and second time varying signal 704, respectively. The dashed line 722 indicates a point in time, tmax1, which is the center of the pulse where dA/dt 712 of the first time varying signal 702 is maximum. The dashed line 724 indicates a point in time, tmax2, which is the center of the pulse where dA/dt 714 of the second time varying signal 704 is maximum. The dashed line 732 indicates a point in time, tmin1, which is the center of the pulse where dA/dt 712 of the first time varying signal 702 is minimum. The dashed line 734 indicates a point in time, tmin2, which is the center of the pulse where dA/dt 714 of the second time varying signal 704 is minimum. As shown in FIG. 7B, tmax1 is not equal to tmax2 and tmin1 is not equal to tmin2 which are indications that the object is not homogeneously colored.

The difference between tmax1, tmax2 and/or the difference between tmin1, tmin2 of the derivative signals 712, 714 can be used as an indication of asymmetrical arrangement of the color regions. The analyzer can determine the symmetry or asymmetry of the color regions based on calculating tmin1−tmin2 and tmax1−tmax2. First and second object color regions are inhomogeneous and are arranged asymmetrically with respect to one another along the flow direction if tmax1−tmax2≠0 and tmin1−tmin2≠0.

Figure 8A:
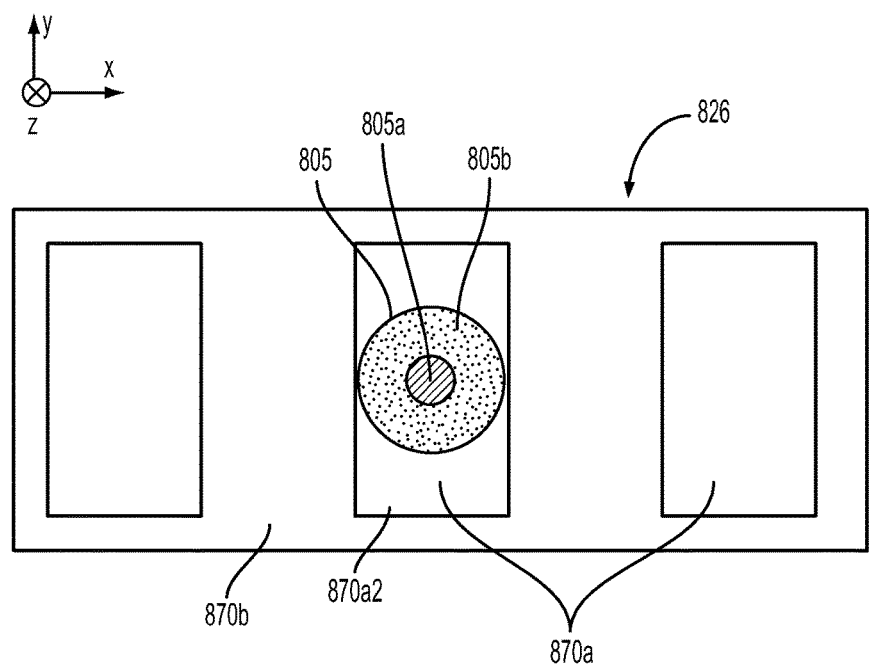
FIG. 8A is a plan view of a spatial filter with an object passing adjacent and traveling relative thereto, the object having a first colored region and a second colored region symmetrically disposed relative to one another.

Turning now to FIG. 8A, object 805 has an inhomogeneous and symmetrical color distribution. FIG. 8A shows object 805 as it travels past more transmissive mask features 870a and less transmissive mask features 870b of spatial filter 826. Light emanating from regions 805a and 805b can be sensed by first and second detectors in a configuration illustrated by FIGS. 1D, 2 and/or 3, for example.

Figure 8B:
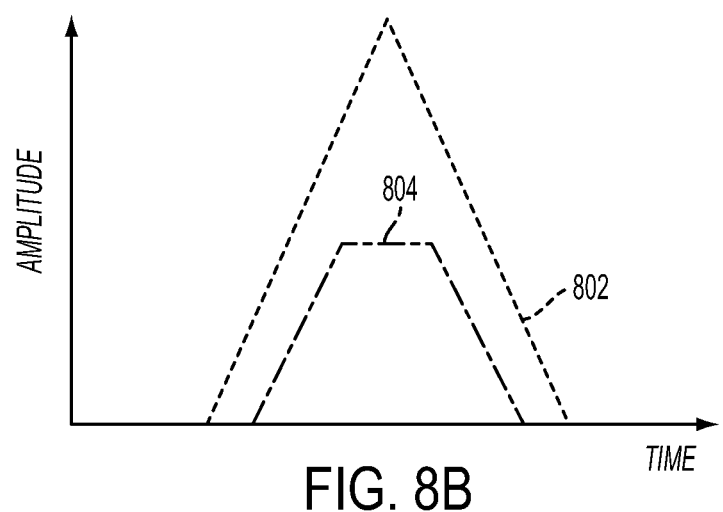
FIG. 8B shows approximated graphs of a first time varying signal and a second time varying signal generated in response to emanating light modulated by one light transmissive region of FIG. 8A.
Figure 8C:
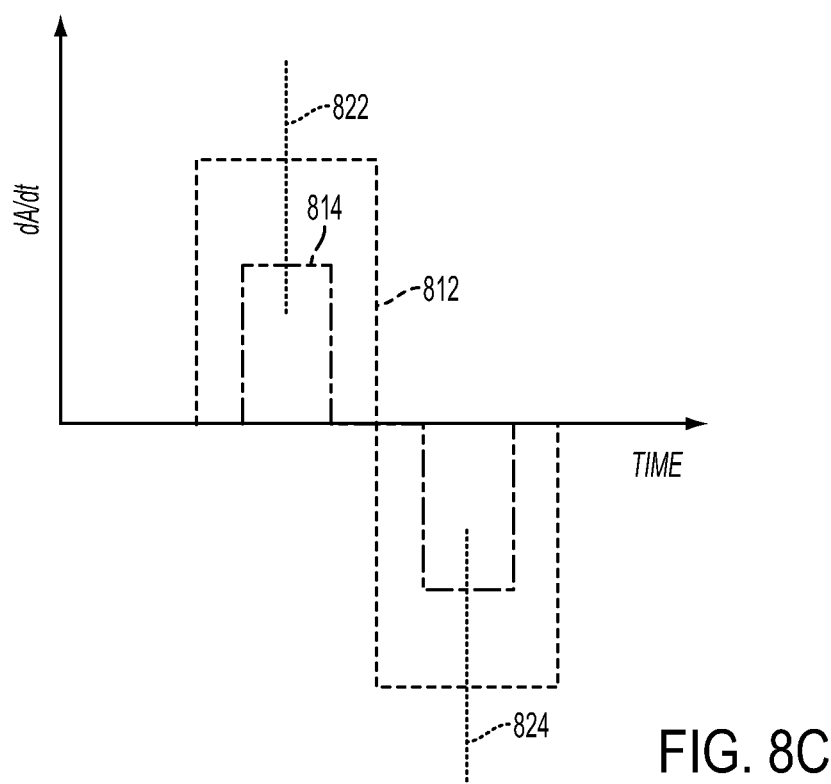
FIG. 8C provides plots of the derivative of the first time varying signal and second time varying signal from FIG. 8B.

FIG. 8B shows a plot of the first time varying signal 802 generated by a first detector in response to light emanating from region 805b and a second time varying signal 804 generated by a second detector in response to light emanating from region 805a as object 805 travels past mask feature 870a2. FIG. 8C shows plots 812, 814 of the amplitude derivatives dA/dt of the first time varying signal 802 and second time varying signal 804 shown in FIG. 8B. The dashed line 822 indicates a point in time, tmax1, which is the center of the pulse where dA/dt 812 of the first time varying signal 802 is maximum. The dashed line 822 also indicates a point in time, tmax2, which is the center of the pulse where dA/dt 814 of the second time varying signal 804 is maximum, i.e., tmax1 substantially equals tmax2. The dashed line 824 indicates a point in time, tmin1, which is the center of the pulse where dA/dt 812 of the first time varying signal 802 is minimum. The dashed line 824 also indicates a point in time, tmin2, which is the center of the pulse where dA/dt 814 of the second time varying signal 804 is minimum, i.e., tmin1 substantially equals tmin2. As shown in FIG. 8C, for color regions that are symmetrically arranged along the direction of travel, the difference between tmax1 and tmax2 and the difference between tmin1 and tmin2 is substantially equal to zero.

Figure 9A:
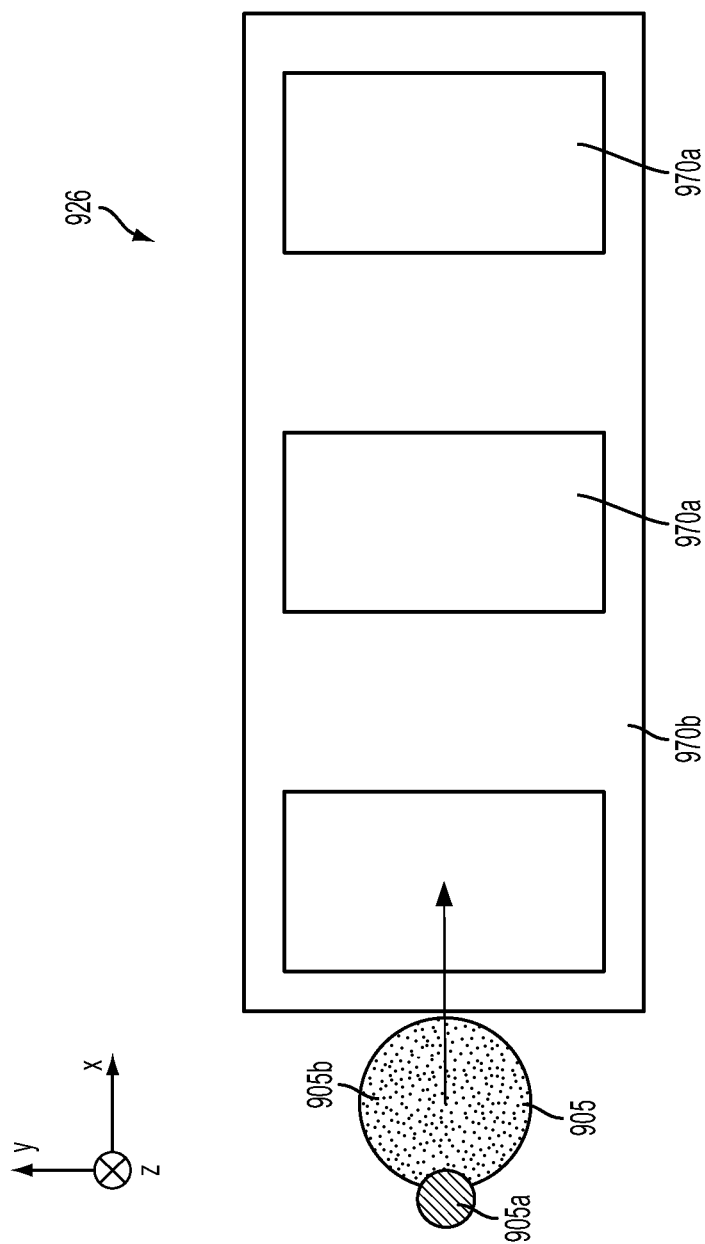
FIG. 9A a plan view of a spatial filter with an object passing adjacent and traveling relative thereto, the object having a first colored region and a second colored at least partially separated from one another.

FIG. 9A shows a portion of a spatial filter 926 having more light transmissive features 970a and less light transmissive features 970b. Two objects 905a and 905b of different colors are moving together generally longitudinally along the x-axis with respect to the spatial filter 926. Thus, object 905a can be considered as a first color region and object 905b can be considered a second color region. In FIG. 9A, the second color region 905b is at least partially separated from the first color region 905a (i.e. a portion of the second color region 905b does not overlap with the first color region 905a in the x-y plane). As the objects 905a and 905b travel relative to the spatial filter 926, the objects 905a and 905b change position relative to mask features 970 including more light transmissive regions 970a and less light transmissive regions 970b. Objects 905a and 905b have light emanating therefrom that is modulated by the mask features 970.

Figure 9B:
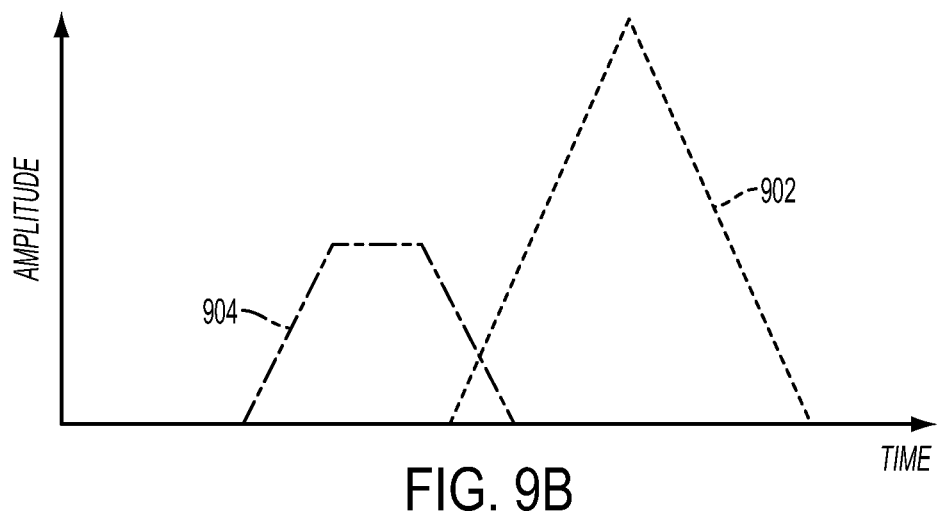
FIG. 9B provides graphs of a first time varying signal and a second time varying signal generated in response to emanating light modulated by one light transmissive region of FIG. 9A.

In configurations as shown in FIGS. 1D, 2, and/or 3, for example, light of a first color emanates from object 905b and is sensed by a first detector and light of a second color emanates from object 905a and is sensed by a second detector. FIG. 9B shows the output signal from the first detector and the output signal from the second detector as the objects 905b, 905a pass a more transmissive mask feature 970a. The first detector generates a first time varying electrical output signal in response to the light sensed from object 905b and the second detector generates a second time varying electrical output signal in response to the light sensed from object 905a. FIG. 9B shows the first time varying signal 902 and second time varying signal 904 generated by the first and second detectors.

Figure 9C:
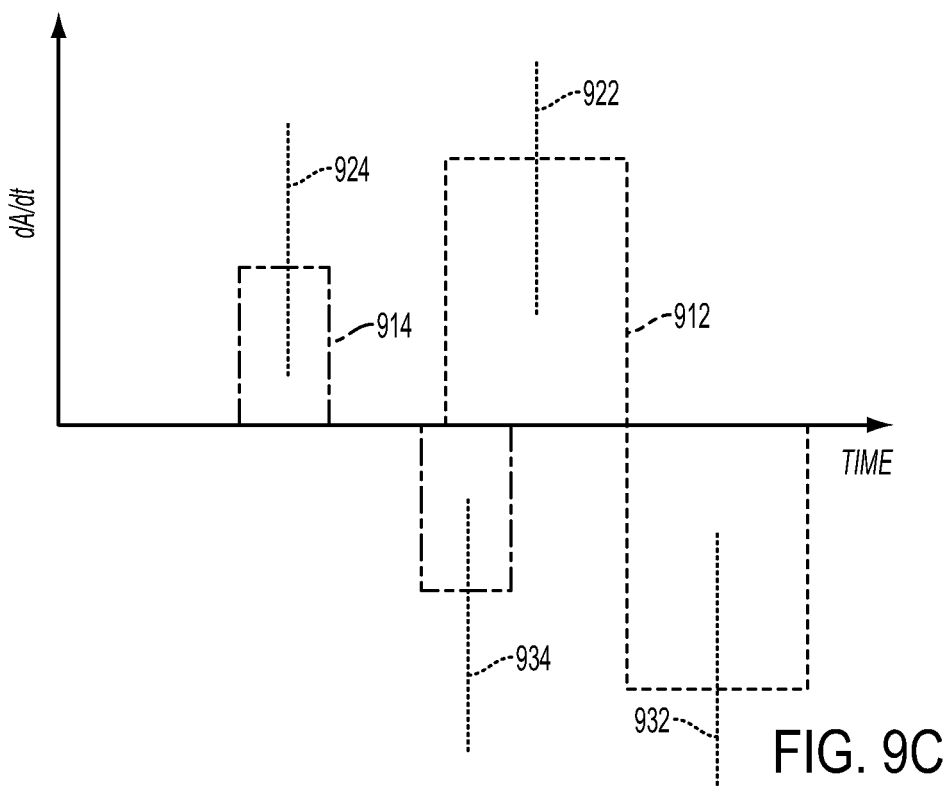
FIG. 9C shows plots of the derivative of the first time varying signal and second time varying signal from FIG. 9B.

FIG. 9C shows a plot 912 of the amplitude derivative dA/dt of the first time varying signal 902 and plot 914 of the amplitude derivative dA/dt of the second time varying signal 904. As shown in FIG. 9C tmax1, indicated by dashed line 922, is time at which the center of the positive going pulse of the derivative signal 912 is maximum; tmax2, indicated by dashed line 924, is the time at which the center of the positive going pulse of the derivative signal 914 is maximum; tmin1, indicated by dashed line 932, is the time at which the center of the negative going pulse of the derivative signal 912 is minimum; and tmin2, indicated by dashed line 934, is the time at which the center of the negative going pulse of derivative signal 914 is minimum. First region (or object) 905a and the second region (or object) 905b are at least partially separated with respect to one another if |tmax1−tmin1|<|tmax1−tmax2|.

Figure 10A:
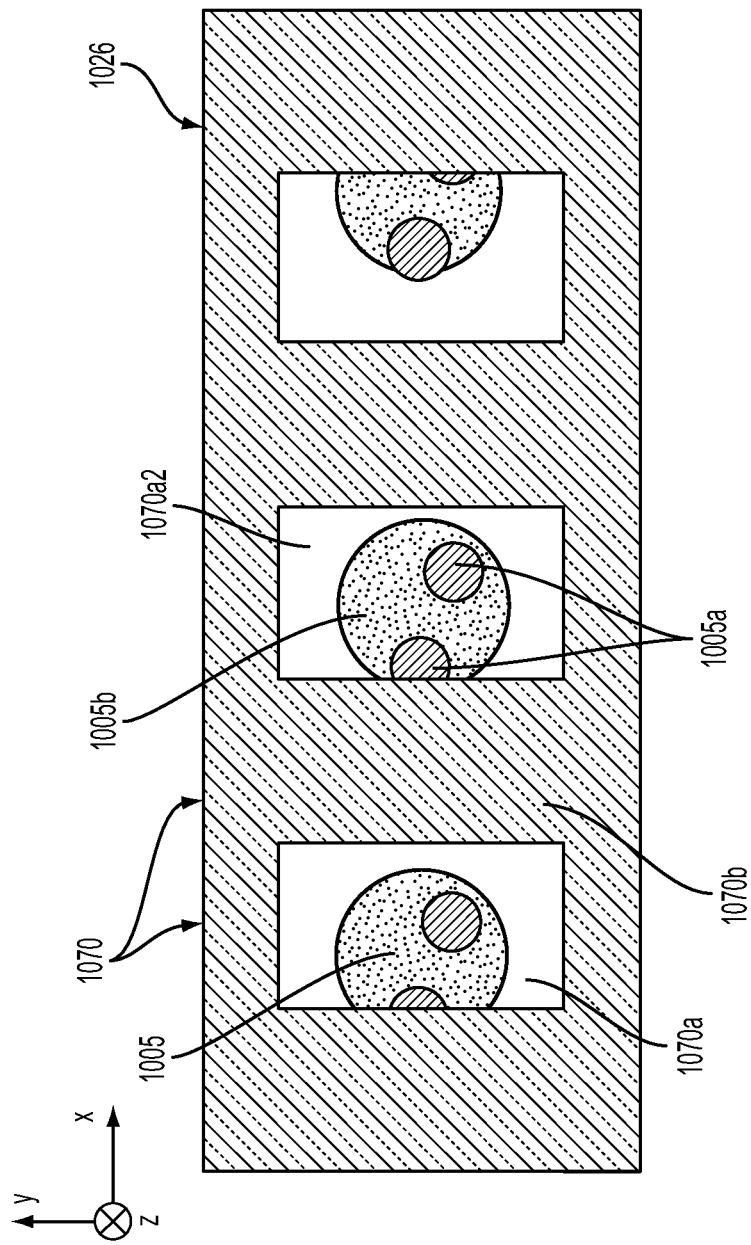
FIG. 10A is a plan view of a spatial filter with an object passing adjacent and traveling relative thereto, the object having a first colored region and two second colored regions granularly disposed within the first colored region.

In some embodiments, the output signals from the first and second detectors includes information about granular color distributions. FIG. 10A shows a portion of a spatial filter 1026 with objects 1005 moving with respect to the spatial filter 1026. The objects 1005 include two granular color regions 1005a and a second color region 1005b. In FIG. 10A, the first color regions 1005a are disposed within the second color region 1005b. As the objects 1005 travel relative to the spatial filter 1026, the objects 1005 change position relative to the more light transmissive mask features 1070a and less light transmissive mask features 1070b. Light emanating from the objects 1005 is modulated by the mask features 1070.

Figure 10B:
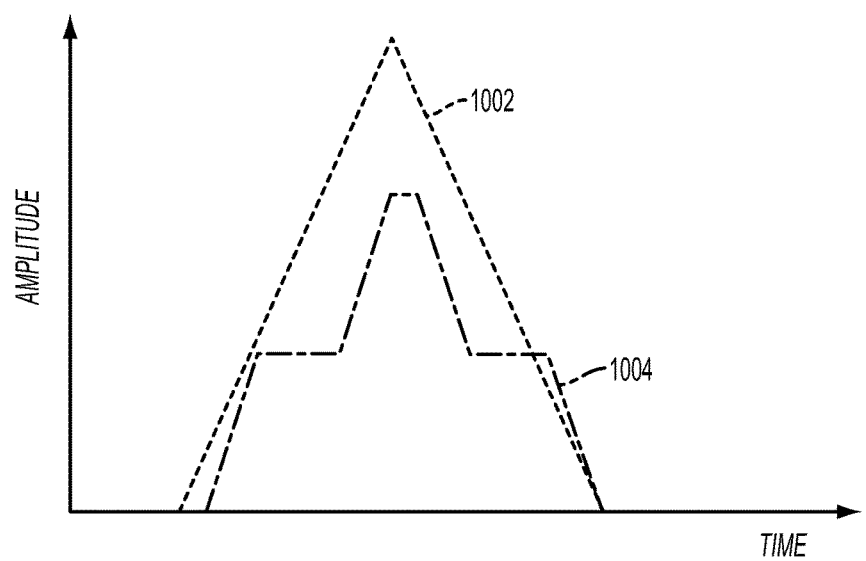
FIG. 10B depicts graphs of a first time varying signal and second time varying signal generated by emanating light modulated by one light transmissive region of FIG. 10A.

In configurations as shown in FIGS. 1D, 2, and/or 3, for example, light of a first color emanates from region 1005b and is sensed by a first detector. Light of a second color emanates from second regions 1005a and is sensed by a second detector. As shown in FIG. 10B, the first detector generates a first time varying electrical output signal 1002 in response to the light sensed from region 1005b and the second detector generates a second time varying electrical output signal 1002 in response to the light sensed from regions 1005a. FIG. 10B shows plots of the first time varying signal 1002 and second time varying signal 1004 as the object 1005, moves past light transmissive region 1070a2 of FIG. 10A.

Figure 10C:
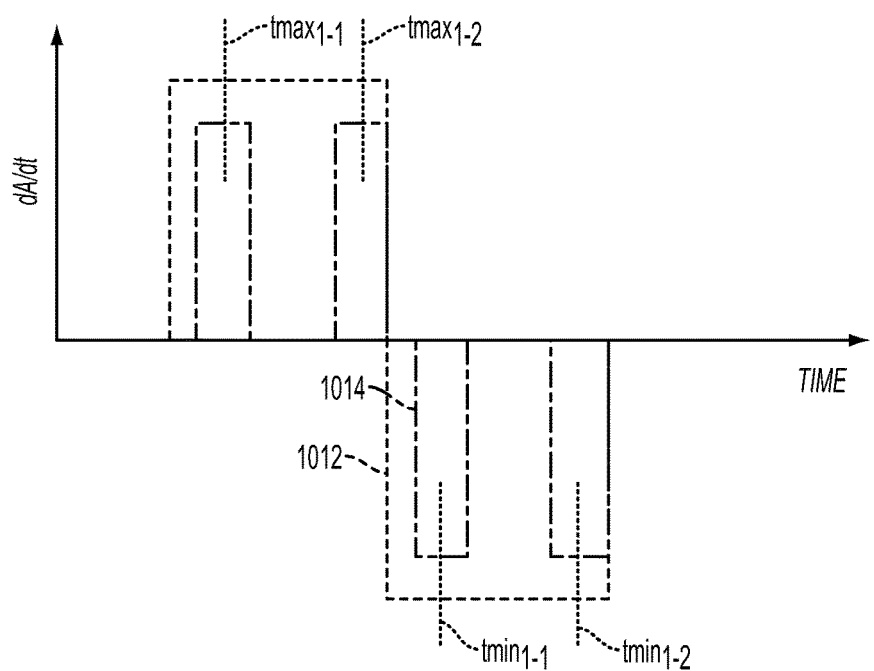
FIG. 10C depicts plots of the derivative of the first time varying signal and second time varying signal from FIG. 10B.

FIG. 10C shows a plot of the amplitude derivative dA/dt 1012 of the first time varying signal 1002 and a plot of the amplitude derivative dA/dt 1014 of the second time varying signal 1004. As shown in FIG. 10C, the multiple occurrences of local maxima, tmax1-1, tmax1-2 and local minima tmin1-1, tmin1-2 in the derivative signal 1012 indicate multiple second color regions 1005a.

Figure 11:
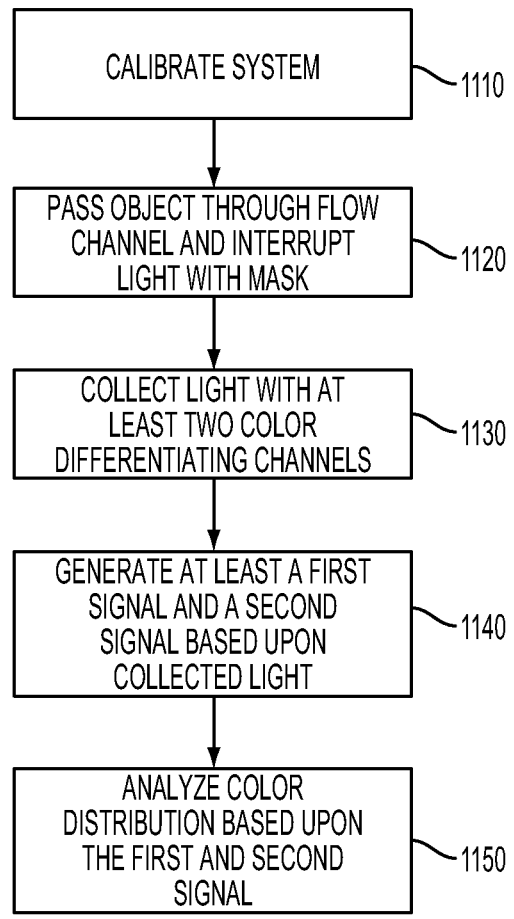
FIG. 11 shows a flow diagram of a method of analyzing a sample according to an example embodiment.

FIG. 11 shows a flow diagram of a method of analyzing a sample. As part of an initialization 1110 for the system, objects of a known velocity and/or size and/or shape and/or depth and/or color distribution (both homogenous and inhomogeneous) and/or luminescence are passed through a flow channel relative to a spatial filter so that the system can be calibrated. Light from the sample containing an object of interest is modulated 1120 by mask features of the spatial filter. The light is sensed 1130 with a first color differentiating detection channel and a second color differentiating detection channel. A first electrical signal is generated 1140 based upon the sensed light that falls within a first wavelength range 1140 and a second electrical signal is generated based upon the sensed light that falls within a second wavelength range. The first and second signals are analyzed 1150 determine a color distribution of the sample.

Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

The invention claimed is:

1. A system, comprising:
a spatial filter having a plurality of mask features and extending along a flow direction, light emanating from at least one object moving along the flow direction, an intensity of the emanating light being time modulated according to the mask features;
a first detector positioned to sense a first portion of the emanating light, the first portion of light having a first wavelength range, the first detector configured to generate a first time varying electrical signal in response to the first portion of light;
a second detector positioned to sense a second portion of the emanating light, the second portion of light having a second wavelength range different from the first wavelength range, the second detector configured to generate a second time varying electrical signal in response to the second portion of light; and an analyzer configured to:
calculate a time-varying difference signal comprising a difference between the first electrical signal and the second electrical signal;
identify a frequency component of the time-varying difference signal;
compare the frequency component of the time varying difference signal to a frequency of the mask features; and
determine homogeneous or inhomogeneous color distribution of the object based on the comparison.

2. The system of claim 1, further comprising at least one of:
a first optical filter arranged in a path of the emanating light and between the object and the first detector, the first optical filter configured to substantially transmit the first wavelength range to the first detector and to substantially block wavelengths other than the first wavelength range from reaching the first detector; and
a second optical filter arranged in a path of the emanating light and between the object and the second detector, the second optical filter configured to substantially transmit the second wavelength range to the second detector and to substantially block wavelengths other than the second wavelength range from reaching the second detector.

3. The system of claim 1, wherein:
the first portion of light comprises light fluorescing from the object; and
the second portion of light comprises light scattered by the object.

4. The system of claim 1, wherein the analyzer is further configured to determine a symmetric spatial distribution of color of the object, an asymmetric spatial distribution of color of the object, a separated spatial distribution of color of the object, and a granular spatial distribution of color of the object.

5. The device of claim 1, wherein the analyzer is configured to calculate at least one of: a depth of a first color region of the object in the flow path based on the first electrical signal; and a depth of a second color region of the object in the flow path based on the second electrical signal.

6. The system of claim 1, wherein the analyzer is configured to calculate the time-varying difference signal by performing a point by point subtraction of the first electrical signal and the second electrical signal.

7. The device of claim 1, wherein the analyzer is configured to calculate at least one of:
a size of a first color region of the object along a direction perpendicular to the flow path based on the first electrical signal; and
a size of a second color region of the object along a direction perpendicular to the flow direction based on the second electrical signal.

8. A system, comprising:
a spatial filter having a plurality of mask features and extending along a flow direction, light emanating from at least one object moving along the flow direction, an intensity of the emanating light being time modulated according to the mask features;
a first detector positioned to sense a first portion of the emanating light, the first portion of light having a first wavelength range, the first detector configured to generate a first time varying electrical signal in response to the first portion of light;
a second detector positioned to sense a second portion of the emanating light, the second portion of light having a second wavelength range different from the first wavelength range, the second detector configured to generate a second time varying electrical signal in response to the second portion of light; and
an analyzer configured to:
develop a first derivative signal comprising a derivative of an amplitude with respect to time of the first electrical signal and a second derivative signal comprising a derivative of an amplitude with respect to time of the second electrical signal;
determine at least one peak time of the first derivative signal and at least one peak time of the second derivative signal; and
calculate a time difference between the peak time of the first derivative signal and the peak time of the second derivative signal; and
determine symmetrical color distribution or asymmetrical color distribution of the object based on the time difference.

9. The device of claim 8, wherein the analyzer is configured to determine that color regions of the object are symmetrical if the time difference is about zero.

10. The device of claim 8, wherein the analyzer is configured to calculate at least one of:
a size of a first color region of the object along a direction perpendicular to the flow path based on the first electrical signal; and
a size of a second color region of the object along a direction perpendicular to the flow direction based on the second electrical signal.

11. The device of claim 8, wherein the analyzer is configured to calculate at least one of:
a depth of a first color region of the object in the flow path based on the first electrical signal;
a depth of a second color region of the object in the flow path based on the second electrical signal.

12. A system, comprising:
a spatial filter having a plurality of mask features and extending along a flow direction, light emanating from at least one object moving along the flow direction, an intensity of the emanating light being time modulated according to the mask features;
a first detector positioned to sense a first portion of the emanating light, the first portion of light having a first wavelength range, the first detector configured to generate a first time varying electrical signal in response to the first portion of light;
a second detector positioned to sense a second portion of the emanating light, the second portion of light having a second wavelength range different from the first wavelength range, the second detector configured to generate a second time varying electrical signal in response to the second portion of light; and
an analyzer configured to:
calculate a time-varying difference signal comprising a difference between the first electrical signal and the second electrical signal;
perform a cross-correlation of the difference signal and a predicted signal of a homogeneously colored object; and
determine an amount of color inhomogeneity of the object based on the cross-correlation.

13. The device of claim 12, wherein the analyzer is configured to calculate at least one of
- a size of a first color region of the object along a direction perpendicular to the flow path based on the first electrical signal; and
- a size of a second color region of the object along a direction perpendicular to the flow direction based on the second electrical signal.

14. The device of claim 12, wherein the analyzer is configured to calculate at least one of:
- a depth of a first color region of the object in the flow path based on the first electrical signal;
- a depth of a second color region of the object in the flow path based on the second electrical signal.

15. A device, comprising:
- a spatial filter having a plurality of mask features and extending along a flow direction, the mask features including first features having a first optical transmission characteristic and second features having a second optical transmission characteristic, light in a first wavelength range emanating from a first color region moving along the flow direction and light in a second wavelength range emanating from a second color region moving along the flow direction, an intensity of the emanating light being modulated according to the first mask features and the second mask features;
- a detector positioned to sense the light emanating from the first and second color regions and to generate a first time-varying electrical output signal in response to the sensed light emanating from the first color region and to generate a second time-varying electrical output signal in response to light emanating from the second color region; and
- an analyzer configured to:
  - develop a first derivative signal comprising a derivative with respect to time of an amplitude of the first time-varying signal and develop a second derivative signal comprising a derivative with respect to time of an amplitude of the second time-varying signal;
  - identify at least one peak of the first derivative signal and at least one peak of the second derivative signal;
  - calculate a time difference between a time of the peak of the first derivative signal and a time of the peak of the second derivative signal; and
  - determine a spatial separation of the first and second color regions based on the time difference.

16. The device of claim 15, wherein the analyzer is configured to calculate at least one of
- a size of the first color region of the object along a direction perpendicular to the flow path based on the first electrical signal; and
- a size of the second color region of the object along a direction perpendicular to the flow direction based on the second electrical signal.

17. The device of claim 15, wherein the analyzer is configured to calculate at least one of:
- a depth of a first color region of the object in the flow path based on the first electrical signal;
- a depth of a second color region of the object in the flow path based on the second electrical signal.

18. A system, comprising:
- a spatial filter having a plurality of mask features and extending along a flow direction, light emanating from at least one object moving along the flow direction, an intensity of the emanating light being time modulated according to the mask features;
- a first detector positioned to sense a first portion of the emanating light, the first portion of light having a first wavelength range, the first detector configured to generate a first time varying electrical signal in response to the first portion of light;
- a second detector positioned to sense a second portion of the emanating light, the second portion of light having a second wavelength range different from the first wavelength range, the second detector configured to generate a second time varying electrical signal in response to the second portion of light; and
- an analyzer configured to:
  - develop a first derivative signal comprising a derivative of an amplitude of the first electrical signal with respect to time and a second derivative signal comprising a derivative of an amplitude of the second electrical signal with respect to time;
  - count a number of local peaks of the first derivative signal that overlap a peak of the second derivative signal; and
  - determine that multiple color regions of the first wavelength range occur within a color region of the second wavelength range if the number of local peaks is greater than one.

19. The device of claim 18, wherein the analyzer is configured to calculate at least one of:
- a size of at least one color region of the object along a direction perpendicular to the flow path; and
- a depth of at least one color region of the object in the flow path along a direction perpendicular to the flow path.

\* \* \* \* \*